(12) United States Patent
Maruyama

(10) Patent No.: US 8,889,336 B2
(45) Date of Patent: Nov. 18, 2014

(54) RADIATION-SENSITIVE RESIN COMPOSITION AND RADIATION-SENSITIVE ACID GENERATING AGENT

(71) Applicant: JSR Corporation, Tokyo (JP)

(72) Inventor: Ken Maruyama, Tokyo (JP)

(73) Assignee: JSR Corporation, Tokyo (JP)

( * ) Notice: Subject to any disclaimer, the term of this patent is extended or adjusted under 35 U.S.C. 154(b) by 0 days.

(21) Appl. No.: 13/905,170

(22) Filed: May 30, 2013

(65) Prior Publication Data

US 2013/0260316 A1 Oct. 3, 2013

Related U.S. Application Data

(63) Continuation of application No. PCT/JP2011/077859, filed on Dec. 1, 2011.

(30) Foreign Application Priority Data

Dec. 2, 2010 (JP) ................. 2010-269555

(51) Int. Cl.
| | | |
|---|---|---|
| *G03F 7/004* | (2006.01) | |
| *G03F 7/028* | (2006.01) | |
| *G03F 7/039* | (2006.01) | |
| *C07C 309/01* | (2006.01) | |
| *C07C 309/06* | (2006.01) | |
| *G03F 7/027* | (2006.01) | |
| *G03F 7/029* | (2006.01) | |
| *C08F 220/10* | (2006.01) | |
| *C08K 5/42* | (2006.01) | |
| *C08L 33/04* | (2006.01) | |
| *G03F 7/20* | (2006.01) | |

(52) U.S. Cl.
CPC ............... *G03F 7/027* (2013.01); *G03F 7/029* (2013.01); *C07C 309/06* (2013.01); *C08F 220/10* (2013.01); *C08K 5/42* (2013.01); *C08L 33/04* (2013.01); *G03F 7/0045* (2013.01); *G03F 7/0046* (2013.01); *G03F 7/0397* (2013.01); *G03F 7/2041* (2013.01); *G03F 7/0392* (2013.01); *Y10S 430/122* (2013.01); *Y10S 430/124* (2013.01); *Y10S 430/126* (2013.01)
USPC ........ 430/270.1; 430/921; 430/923; 430/925; 562/30

(58) Field of Classification Search
USPC .................. 430/270.1, 921, 923, 925; 562/30
See application file for complete search history.

(56) References Cited

U.S. PATENT DOCUMENTS

| | | | |
|---|---|---|---|
| 2008/0182203 A1 | 7/2008 | Yun et al. | |
| 2009/0023095 A1* | 1/2009 | Hada et al. ................ | 430/281.1 |
| 2010/0015553 A1* | 1/2010 | Shimizu et al. ........... | 430/281.1 |
| 2010/0136478 A1 | 6/2010 | Kawaue et al. | |
| 2010/0304303 A1* | 12/2010 | Maeda et al. ............. | 430/286.1 |
| 2012/0015299 A1* | 1/2012 | Komuro et al. ........... | 430/285.1 |

FOREIGN PATENT DOCUMENTS

| | | | |
|---|---|---|---|
| JP | 2002-145955 | 5/2002 | |
| JP | 2002-201232 | 7/2002 | |
| JP | 2002-363123 | 12/2002 | |
| JP | 2008-007409 | 1/2008 | |
| JP | 2008-007410 | 1/2008 | |
| JP | 2010-113209 | 5/2010 | |
| JP | 2010-256872 | 11/2010 | |
| WO | WO 2008/047678 | 4/2008 | |
| WO | WO 2009/051088 | 4/2009 | |
| WO | WO 2009/057769 | * 5/2009 | |

OTHER PUBLICATIONS

International Search Report for corresponding International Application No. PCT/JP2011/077859, Dec. 27, 2011.

* cited by examiner

*Primary Examiner* — Anca Eoff
(74) *Attorney, Agent, or Firm* — Oblon, Spivak, McClelland, Maier & Neustadt, L.L.P.

(57) ABSTRACT

A radiation-sensitive resin composition includes a compound represented by a formula (1), and a base polymer. A represents —CO— or —CH$_2$—. R$^1$ represents a hydrocarbon group having 1 to 30 carbon atoms, a heterocyclic group having 3 to 30 ring atoms, or a combination of a first group and a second group. The first group is —CO—, —COO—, —OCO—, —O—CO—O—, —NHCO—, —CONH—, —NH—CO—O—, —O—CO—NH—, —NH—, —S—, —SO—, —SO$_2$—, —SO$_2$—O— or a combination thereof, and the second group is a hydrocarbon group having 1 to 30 carbon atoms, a heterocyclic group having 3 to 30 ring atoms or a combination thereof. A part or all of hydrogen atoms included in the hydrocarbon group and the heterocyclic group are not substituted or substituted. M$^+$ represents a monovalent cation.

(1)

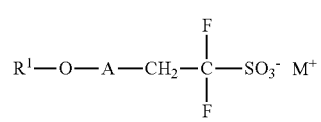

8 Claims, No Drawings

RADIATION-SENSITIVE RESIN COMPOSITION AND RADIATION-SENSITIVE ACID GENERATING AGENT

CROSS-REFERENCE TO RELATED APPLICATIONS

The present application is a continuation application of International Application No. PCT/JP2011/077859, filed Dec. 1, 2011, which claims priority to Japanese Patent Application No. 2010-269555, filed Dec. 2, 2010. The contents of these applications are incorporated herein by reference in their entirety.

BACKGROUND OF THE INVENTION

1. Field of the Invention

The present invention relates to a radiation-sensitive resin composition and a radiation-sensitive acid generating agent.

2. Discussion of the Background

In the field of microfabrication typified by production of integrated circuit devices, lithography techniques have been recently required that enable microfabrication to give a line width of no greater than 100 nm using a far ultraviolet ray such as a KrF excimer laser, an ArF excimer laser, an $F_2$ excimer laser or an EUV (extreme ultraviolet) ray, an X-ray such as a synchrotron radioactive ray, a charged particle ray such as an electron beam, or the like in order to achieve higher integrity. As radiation-sensitive resin compositions suited for such radioactive rays, a number of chemically amplified radiation-sensitive compositions have been proposed in which a chemical amplification effect is utilized which results from a component having an acid-labile group and an acid generating agent that generates an acid by irradiation with a radioactive ray. For example, a polymer compound for photoresist containing a polymer that includes a monomer unit having a norbornane ring-derived group has been known (see Japanese Unexamined Patent Application, Publication No. 2002-201232, and Japanese Unexamined Patent Application, Publication No. 2002-145955). Moreover, in order to improve sensitivity and resolution, a radiation-sensitive resin composition has been disclosed which contains: a polymer having an acid-labile group; and an acid generating agent, and additionally a photoactive compound (see Japanese Unexamined Patent Application, Publication No. 2002-363123).

However, in the field of semiconductors, etc., higher integrity has been desired, and a radiation-sensitive resin composition for forming a resist film has been expected to have higher lithography performances, and also has been required to be superior in a balance of resistance to pattern collapse after development, LWR (Line Width Roughness) and MEEF (Mask Error Enhancement Factor).

SUMMARY OF THE INVENTION

According to one aspect of the present invention, a radiation-sensitive resin composition includes a compound represented by a formula (1), and a base polymer.

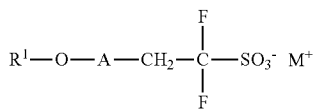

In the formula (1), A represents —CO— or —CH$_2$—. $R^1$ represents a hydrocarbon group having 1 to 30 carbon atoms, a heterocyclic group having 3 to 30 ring atoms, or a combination of a first group and a second group. The first group is —CO—, —COO—, —OCO—, —O—CO—O—, —NHCO—, —CONH—, —NH—CO—O—, —O—CO—NH—, —NH—, —S—, —SO—, —SO$_2$—, —SO$_2$—O— or a combination thereof, and the second group is a hydrocarbon group having 1 to 30 carbon atoms, a heterocyclic group having 3 to 30 ring atoms or a combination thereof. A part or all of hydrogen atoms included in the hydrocarbon group and the heterocyclic group are not substituted or substituted. $M^+$ represents a monovalent cation.

According to another aspect of the present invention, a radiation-sensitive acid generating agent includes a compound represented by a formula (1).

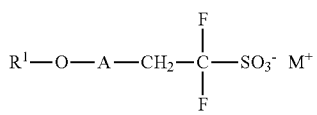

In the formula (1), A represents —CO— or —CH$_2$—. $R^1$ represents a hydrocarbon group having 1 to 30 carbon atoms, a heterocyclic group having 3 to 30 ring atoms, or a combination of a first group and a second group. The first group is —CO—, —COO—, —OCO—, —O—CO—O—, —NHCO—, —CONH—, —NH—CO—O—, —O—CO—NH—, —NH—, —S—, —SO—, —SO$_2$—, —SO$_2$—O— or a combination thereof, and the second group is a hydrocarbon group having 1 to 30 carbon atoms, a heterocyclic group having 3 to 30 ring atoms or a combination thereof. A part or all of hydrogen atoms included in the hydrocarbon group and the heterocyclic group are not substituted or substituted. $M^+$ represents a monovalent cation.

DESCRIPTION OF THE EMBODIMENTS

According to an embodiment of the present invention, a radiation-sensitive resin composition contains:
(A) a compound represented by the following formula (1); and
(B) a base polymer.

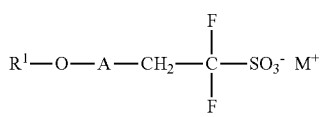

wherein, in the formula (1), A represents —CO— or —CH$_2$—; $R^1$ represents a hydrocarbon group having 1 to 30 carbon atoms, a heterocyclic group having 3 to 30 ring atoms, or a group derived by combining —CO—, —COO—, —OCO—, —O—CO—O—, —NHCO—, —CONH—, —NH—CO—O—, —O—CO—NH—, —NH—, —S—, —SO—, —SO$_2$—, —SO$_2$—O— or a combination thereof with a hydrocarbon group having 1 to 30 carbon atoms, a heterocyclic group having 3 to 30 ring atoms or a combination thereof, wherein a part or all of hydrogen atoms included in the hydrocarbon group and the heterocyclic group are not substituted or substituted; and M$^+$ represents a monovalent cation.

R$^1$ in the above formula (1) is preferably represented by the following formula (a1):

wherein, in the formula (a1), R$^2$ represents a chain hydrocarbon group having 1 to 30 carbon atoms, an alicyclic hydrocarbon group having 3 to 30 carbon atoms or a heterocyclic group having 3 to 30 ring atoms; R$^3$ and R$^5$ each independently represent —CO—, —COO—, —OCO—, —O—CO—O—, —NHCO—, —CONH—, —NH—CO—O—, —O—CO—NH—, —NH—, —S—, —SO—, —SO$_2$—, —SO$_2$—O— or a combination thereof; R$^4$ represents a hydrocarbon group having 1 to 30 carbon atoms; m is an integer of 0 to 2; n is 0 or 1, wherein a part or all of hydrogen atoms included in the chain hydrocarbon group, the alicyclic hydrocarbon group and the heterocyclic group represented by R$^2$, and the hydrocarbon group represented by R$^4$ are not substituted or substituted, and wherein in the case where m is 2, a plurality of R$^3$s are each identical or different and a plurality of R$^4$s are each identical or different; and * denotes a binding site to —O— in the above formula (1).

M$^+$ in the above formula (1) preferably represents a sulfonium cation or an iodonium cation.

The base polymer (B) is preferably a polymer that includes a structural unit represented by the following formula (2):

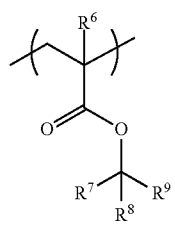

wherein, in the formula (2), R$^6$ represents a hydrogen atom or a methyl group; R$^7$ represents a linear or branched alkyl group having 1 to 4 carbon atoms, or an alicyclic hydrocarbon group having 4 to 20 carbon atoms; and R$^8$ and R$^9$ each independently represent a linear or branched alkyl group having 1 to 4 carbon atoms, or an alicyclic hydrocarbon group having 4 to 20 carbon atoms, or R$^8$ and R$^9$ bond to one another to taken together represent an alicyclic hydrocarbon group having 4 to 20 carbon atoms together with the carbon atom to which R$^8$ and R$^9$ bond.

The radiation-sensitive acid generating agent of the embodiment of the present invention includes a compound represented by the following formula (1):

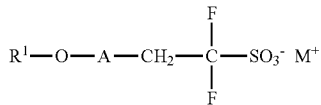

wherein, in the formula (1), A represents —CO— or —CH$_2$—; R$^1$ represents a hydrocarbon group having 1 to 30 carbon atoms, a heterocyclic group having 3 to 30 ring atoms, or a group derived by combining —CO—, —COO—, —OCO—, —O—CO—O—, —NHCO—, —CONH—, —NH—CO—O—, —O—CO—NH—, —NH—, —S—, —SO—, —SO$_2$—, —SO$_2$—O— or a combination thereof with a hydrocarbon group having 1 to 30 carbon atoms, a heterocyclic group having 3 to 30 ring atoms or a combination thereof, wherein a part or all of hydrogen atoms included in the hydrocarbon group and the heterocyclic group are not substituted or substituted; and M$^+$ represents a monovalent cation.

In the compound represented by the above formula (1) included in the radiation-sensitive acid generating agent of the embodiment of the present invention, R$^1$ is preferably represented by the following formula (a1):

wherein, in the formula (a1), R$^2$ represents a chain hydrocarbon group having 1 to 30 carbon atoms, an alicyclic hydrocarbon group having 3 to 30 carbon atoms or a heterocyclic group having 3 to 30 ring atoms; R$^3$ and R$^5$ each independently represent —CO—, —COO—, —OCO—, —O—CO—O—, —NHCO—, —CONH—, —NH—CO—O—, —O—CO—NH—, —NH—, —S—, —SO—, —SO$_2$—, —SO$_2$—O— or a combination thereof; R$^4$ represents a hydrocarbon group having 1 to 30 carbon atoms; m is an integer of 0 to 2; n is 0 or 1, wherein a part or all of hydrogen atoms included in the chain hydrocarbon group, the alicyclic hydrocarbon group and the heterocyclic group represented by R$^2$, and the hydrocarbon group represented by R$^4$ are not substituted or substituted, and wherein in the case where m is 2, a plurality of R$^3$s are each identical or different and a plurality of R$^4$s are each identical or different; and * denotes a binding site to —O— in the above formula (1).

The radiation-sensitive resin composition of the embodiment of the present invention is superior in transparency and sensitivity to far ultraviolet rays typified by a KrF excimer laser, an ArF excimer laser, an F$_2$ excimer laser and EUV, and to actinic radioactive rays such as an electron beam, and also has a favorable balance of resistance to pattern collapse after development, LWR and MEEF. Moreover, according to the radiation-sensitive acid generating agent of the embodiment of the present invention, a balance of resistance to pattern collapse after development, LWR and MEEF can be improved when used in a radiation-sensitive resin composition.

Hereinafter, the embodiments will now be described in detail, but the present invention is not limited to the following embodiments.

Radiation-Sensitive Resin Composition

The radiation-sensitive resin composition of the embodiment of the present invention contains (A) a compound, and (B) a base polymer as essential components. The radiation-sensitive resin compound may contain a crosslinking agent, (C) a fluorine atom-containing polymer (hereinafter, may be also referred to as "polymer (C)"), an acid diffusion control agent, and other optional component(s) in addition to the compound (A) and the base polymer (B), as long as the effects of the embodiment of the present invention are not impaired. Hereinafter, each component will be described in detail.

(A) Compound

The compound (A) is represented by the above formula (1). The compound (A) generates a compound represented by $R^1$—O-A-CH$_2$—CF$_2$—SO$_3$H upon irradiation with an actinic radioactive ray, and thus may be suitably used in the radiation-sensitive resin composition as a radiation-sensitive acid generating agent.

In the above formula (1), A represents —CO— or —CH$_2$—; $R^1$ represents a hydrocarbon group having 1 to 30 carbon atoms, a heterocyclic group having 3 to 30 ring atoms, or a group derived by combining —CO—, —COO—, —OCO—, —O—CO—O—, —NHCO—, —CONH—, —NH—CO—O—, —O—CO—NH—, —NH—, —S—, —SO—, —SO$_2$—, —SO$_2$—O— or a combination thereof with a hydrocarbon group having 1 to 30 carbon atoms, a heterocyclic group having 3 to 30 ring atoms or a combination thereof, wherein a part or all of hydrogen atoms included in the hydrocarbon group and the heterocyclic group are not substituted or substituted; and $M^+$ represents a monovalent cation.

$R^1$ is preferably a group represented by the above formula (a1). In the above formula (a1), $R^2$ represents a chain hydrocarbon group having 1 to 30 carbon atoms, an alicyclic hydrocarbon group having 3 to 30 carbon atoms or a heterocyclic group having 3 to 30 ring atoms; $R^3$ and $R^5$ each independently represent —CO—, —COO—, —OCO—, —O—CO—O—, —NHCO—, —CONH—, —NH—CO—O—, —O—CO—NH—, —NH—, —S—, —SO—, —SO$_2$—, SO$_2$—O— or a combination thereof; $R^4$ represents a hydrocarbon group having 1 to 30 carbon atoms; m is an integer of 0 to 2; n is 0 or 1, wherein a part or all of hydrogen atoms included in the chain hydrocarbon group, the alicyclic hydrocarbon group and the heterocyclic group represented by $R^2$, and the hydrocarbon group represented by $R^4$ are not substituted or substituted, and wherein in the case where m is 2, a plurality of $R^3$s are each identical or different and a plurality of $R^4$s are each identical or different; and * denotes a binding site to —O— in the above formula (1).

Examples of preferred groups as the chain hydrocarbon group having 1 to 30 carbon atoms represented by $R^2$ include a methyl group, an ethyl group, a 1-propyl group, a 2-propyl group, a 1-butyl group, a 2-butyl group, a 2-(2-methylpropyl) group, a 1-pentyl group, a 2-pentyl group, a 3-pentyl group, a 1-(2-methylbutyl) group, a 1-(3-methylbutyl) group, a 2-(2-methylbutyl) group, a 2-(3-methylbutyl) group, a neopentyl group, a 1-hexyl group, a 2-hexyl group, a 3-hexyl group, a 1-(2-methylpentyl) group, a 1-(3-methylpentyl) group, a 1-(4-methylpentyl) group, a 2-(2-methylpentyl) group, a 2-(3-methylpentyl) group, a 2-(4-methylpentyl) group, a 3-(2-methylpentyl) group, and a 3-(3-methylpentyl) group. Of these, a 2-propyl group is more preferred.

Examples of preferred groups as the alicyclic hydrocarbon group having 3 to 30 carbon atoms represented by $R^2$ include a cyclopentyl group, a cyclohexyl group, a cycloheptyl group, a 2-norbornyl group, a 1-adamantyl group, and a 2-adamantyl group. Of these, a cyclohexyl group, and an adamantyl group are more preferred.

Examples of preferred groups as the heterocyclic group having 3 to 30 ring atoms represented by $R^2$ include groups having: a lactone structure such as butyrolactone, valerolactone, cyclohexanelactone or norbornanelactone; a cyclic carbonate structure represented by the following formula (a-1) or the like; a cyclic ketone structure represented by the following formulae (b-1) to (b-7) or the like; a cyclic sulfide structure represented by the following formulae (c-1) to (c-4) or the like; a structure represented by the following formula (d-1). Of these, groups having a norbornane lactone structure, and groups having a structure represented by the following formula (d-1) are more preferred, and groups having a norbornane lactone structure are still more preferred.

(a-1)

(b-1)

(b-2)

(b-3)

(b-4)

(b-5)

(b-6)

(b-7)

(c-1)

(c-2)

(c-3)

-continued

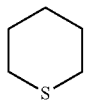
(c-4)

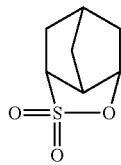
(d-1)

$R^3$ and $R^5$ preferably represent —CO—, —COO—, —OCO—, —NHCO—, or —CONH—.

The hydrocarbon group having 1 to 30 carbon atoms represented by $R^4$ is exemplified by a chain hydrocarbon group having 1 to 30 carbon atoms, an alicyclic hydrocarbon group having 3 to 30 carbon atoms, and the like. Examples of preferred group as these groups include those derived from the group exemplified as each of the groups which may be represented by $R^2$ by removing one hydrogen atom. Among these, a methylene group, a norbornylene group and a cyclohexylene group are more preferred.

In addition, examples of the substituent in $R^2$ and $R^4$ include a hydroxyl group, a carboxyl group, a carbonyl group, a nitro group, an amino group, a silyl group, a halogen atom, a thienyl group, and the like. In addition, in the case in which $R^2$ and $R^4$ represent a chain hydrocarbon group, a monovalent alicyclic hydrocarbon group may be included as a substituent, whereas in the case in which $R^2$ and $R^4$ represent an alicyclic hydrocarbon group, a monovalent chain hydrocarbon group may be included as a substituent.

$M^+$ in the above formula (1) preferably represents a sulfonium cation or an iodonium cation.

Sulfonium Cation

The sulfonium cation is preferably a sulfonium cation which is included in the compound (A) and is represented by the following formula (4a) or the following formula (4b). It is to be noted that the sulfonium salts represented by the following formulae (4a) and (4b) are included in preferred compounds (A) in the embodiment of the present invention.

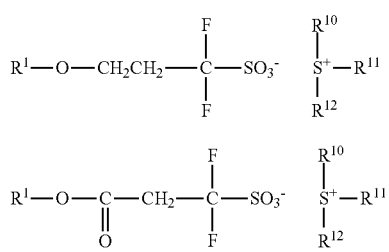

In the above formula, $R^1$ is as defined in the above formula (1); $R^{10}$, $R^{11}$ and $R^{12}$ each independently represent a linear or branched alkyl group having 1 to 10 carbon atoms, an alkenyl group having 1 to 10 carbon atoms, an oxoalkyl group having 1 to 10 carbon atoms, an aryl group having 6 to 18 carbon atoms, an aralkyl group having 6 to 18 carbon atoms or an aryloxoalkyl group having 6 to 18 carbon atoms, and optionally any two or more among $R^{10}$, $R^{11}$ and $R^{12}$ bond to one another to taken together represent a ring together with the sulfur atom in the formula, wherein a part or all of hydrogen atoms included in the alkyl group, the alkenyl group, the oxoalkyl group, the aryl group, the aralkyl group and the aryloxoalkyl group are not substituted or substituted.

Preferred sulfonium cation in the above formula (4a) and (4b) is exemplified by sulfonium cations represented by the following formulae (4-1) and (4-2).

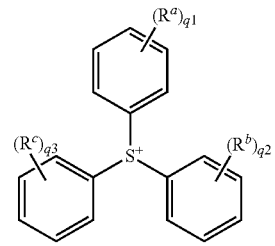
(4-1)

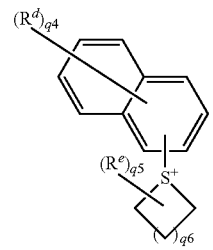
(4-2)

In the above formula (4-1), $R^a$ to $R^c$ each independently represent a hydroxy group, a halogen atom, an alkyl group, a cycloalkyl group, an alkoxy group, a —S—R group or a —SO$_2$—R' group; R represents an alkyl group or an aryl group; R' represents an alkyl group, a cycloalkyl group, an alkoxy group or an aryl group, wherein a part or all of hydrogen atoms included in the alkyl group, the cycloalkyl group, the alkoxy group and the aryl group are not substituted or substituted; $q^1$ to $q^3$ are an integer of 0 to 5, wherein in the case where $q^1$ to $q^3$ are each 2 or greater, a plurality of $R^a$s are each identical or different, a plurality of $R^b$s are each identical or different and a plurality of $R^c$s are each identical or different.

In the above formula (4-2), $R^d$ represents a hydrogen atom, a linear or branched alkyl group having 1 to 8 carbon atoms, or an aryl group having 6 to 8 carbon atoms; $R^e$ represents a hydrogen atom, a linear or branched alkyl group having 1 to 7 carbon atoms, or an aryl group having 6 to 7 carbon atoms, wherein a part or all of hydrogen atoms included in the alkyl group and the aryl group represented by $R^d$ and $R^e$ are not substituted or substituted; $q^4$ is an integer of 0 to 7; $q^5$ is an integer of 0 to 6; and $q^6$ is an integer of 0 to 3, wherein in the case where $q^4$ is 2 or greater, a plurality of $R^d$s are each identical or different, or two or more $R^d$s optionally bond to one another to taken together represent a ring, and wherein in the case where $q^5$ is 2 or greater, a plurality of $R^e$s are each identical or different, and optionally two or more $R^e$s bond to one another to taken together represent a ring.

Specific examples of more preferred sulfonium cation may include those represented by the following formulae (i-1) to (i-67), in addition to the sulfonium cations other than those represented by the above formulae (4-1) and (4-2).

(i-1)
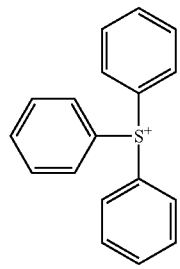
(i-2)
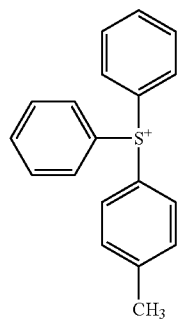
(i-3)
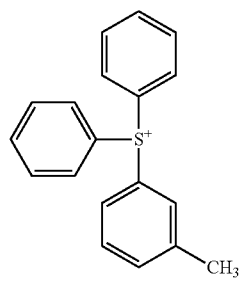
(i-4)
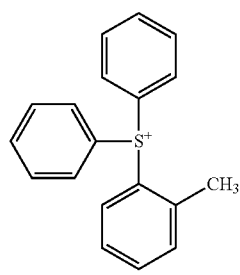
(i-5)
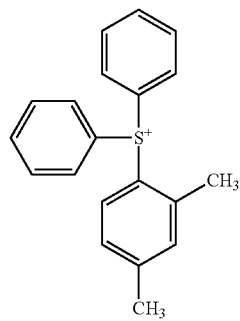
-continued
(i-6)
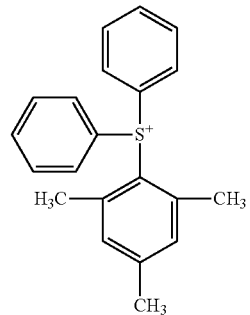
(i-7)
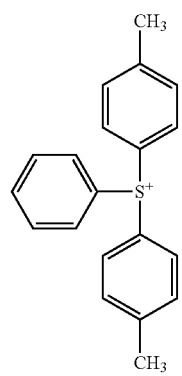
(i-8)
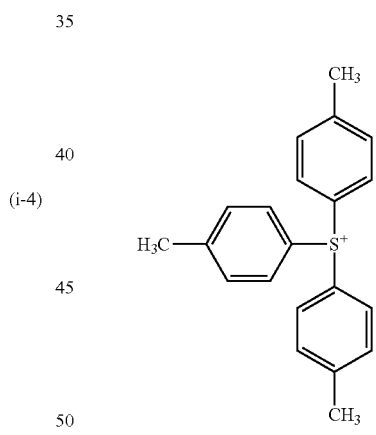
(i-9)
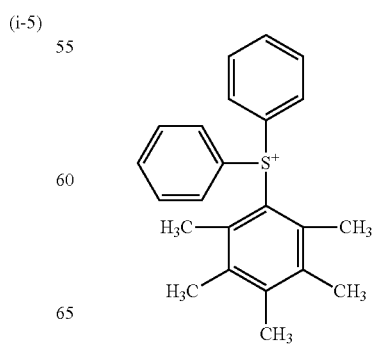

(i-10)
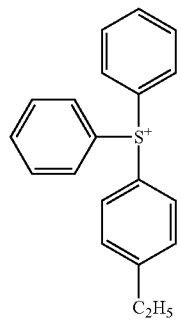
(i-11)
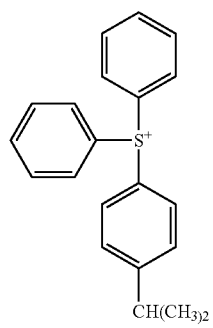
(i-12)
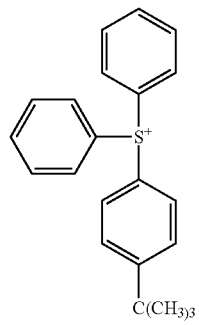
(i-13)
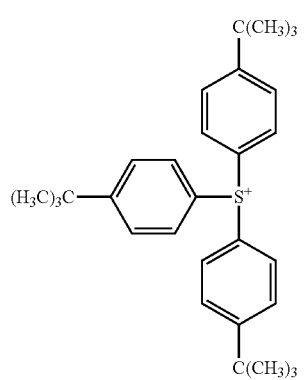
(i-14)
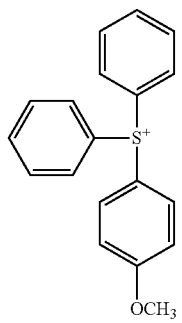
(i-15)
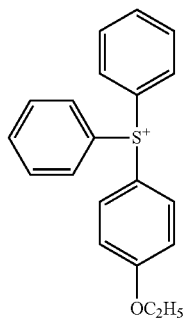
(i-16)
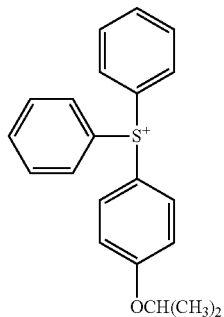
(i-17)
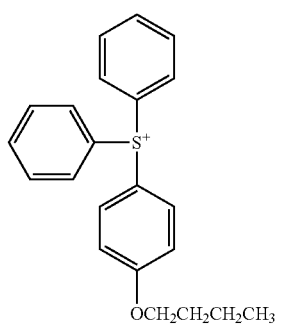
(i-18)
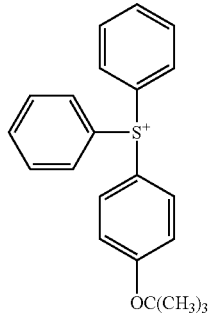

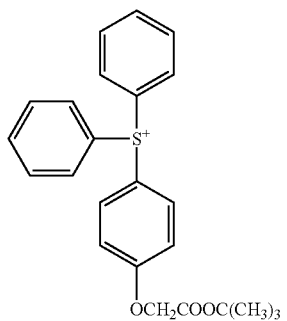
(i-19)
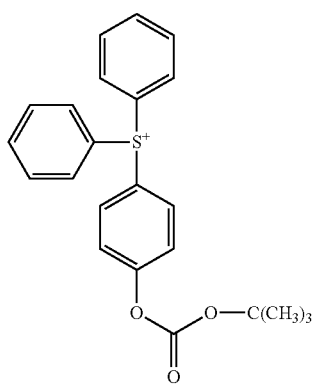
(i-20)
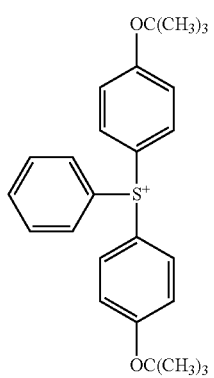
(i-21)
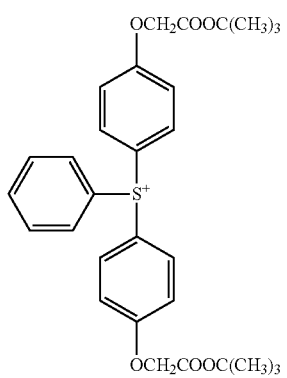
(i-22)
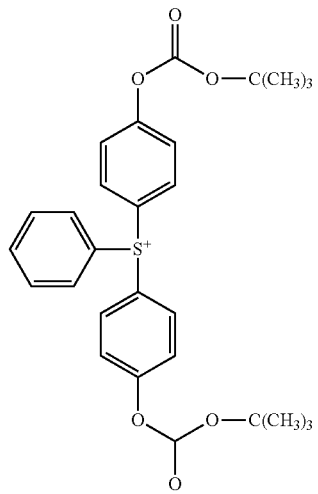
(i-23)
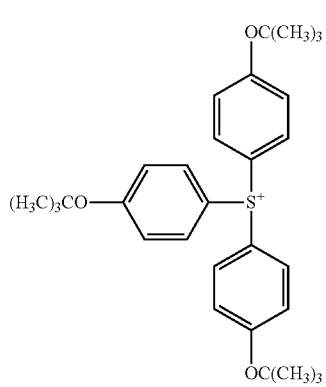
(i-24)
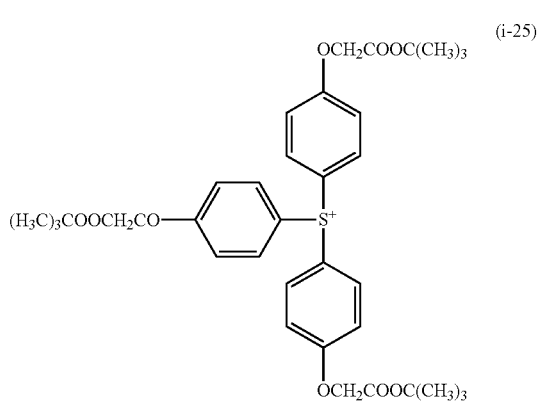
(i-25)

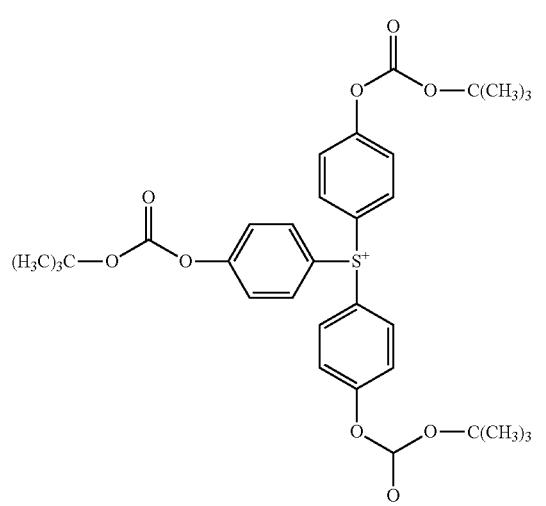
(i-26)
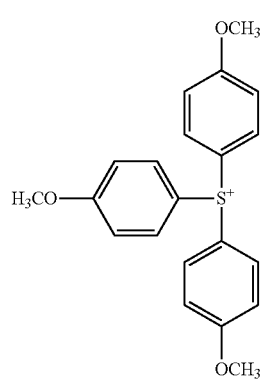
(i-27)
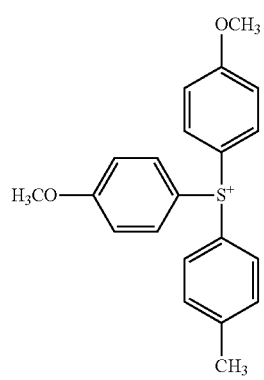
(i-28)
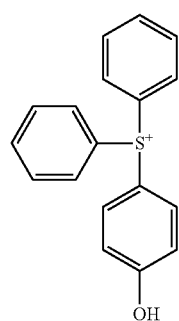
(i-29)
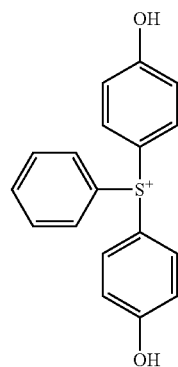
(i-30)
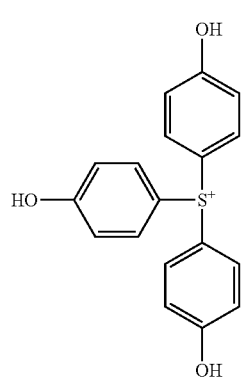
(i-31)
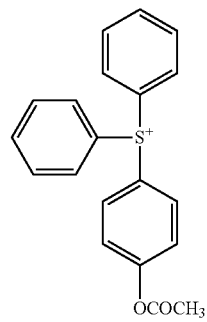
(i-32)
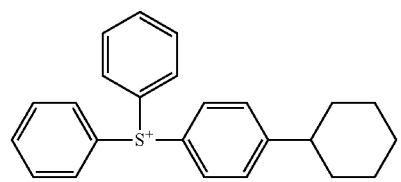
(i-33)
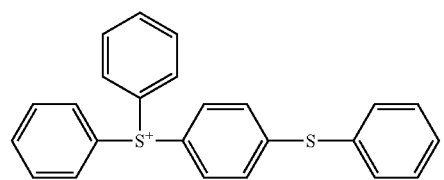
(i-34)

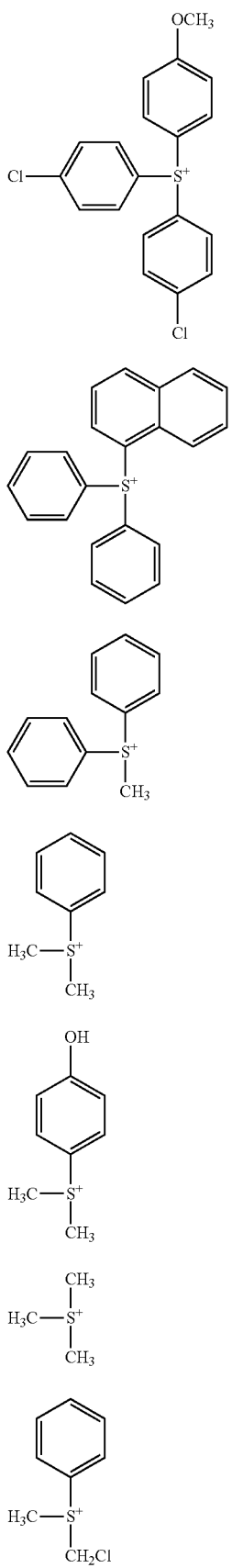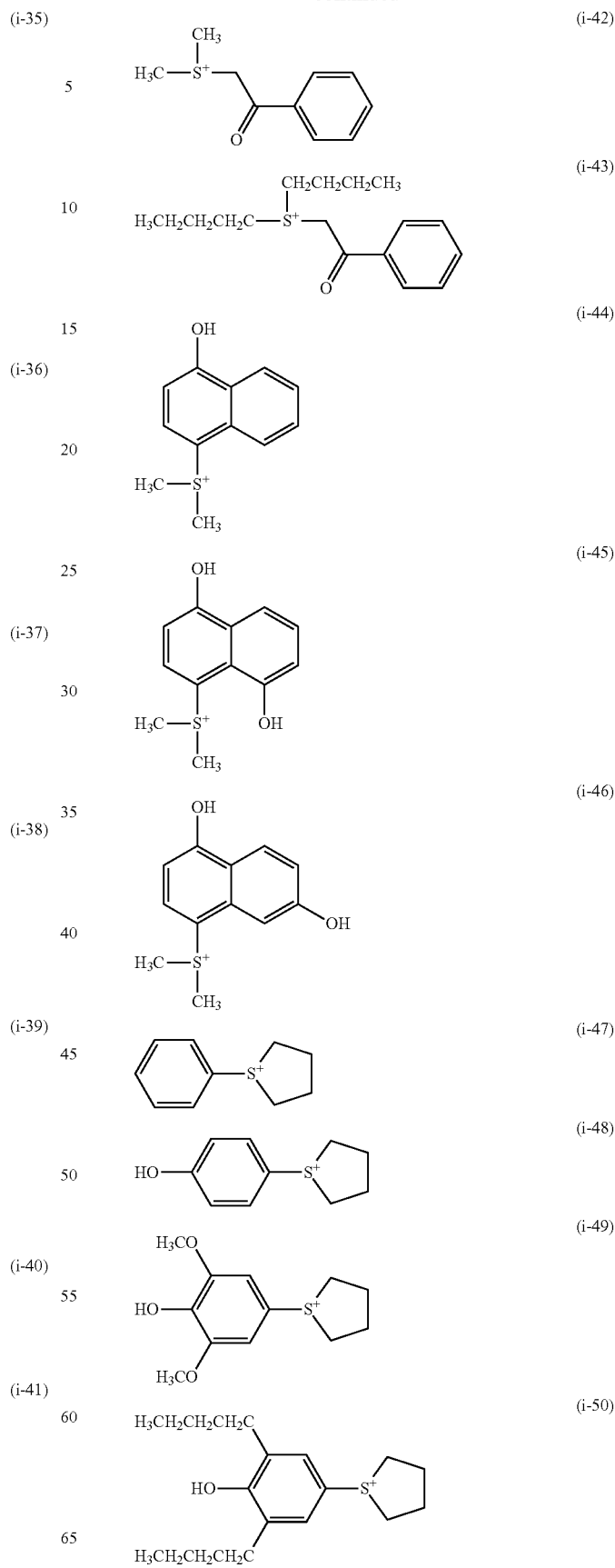

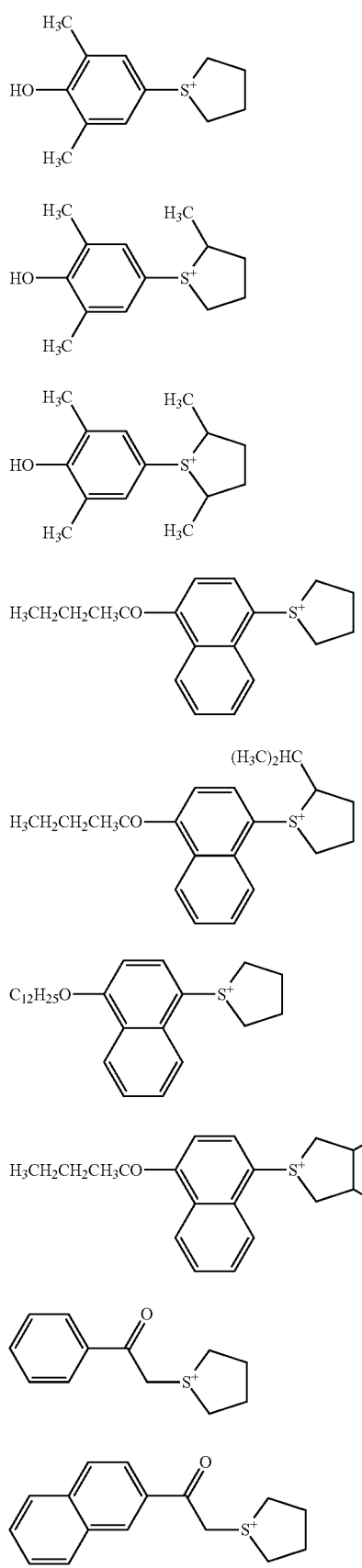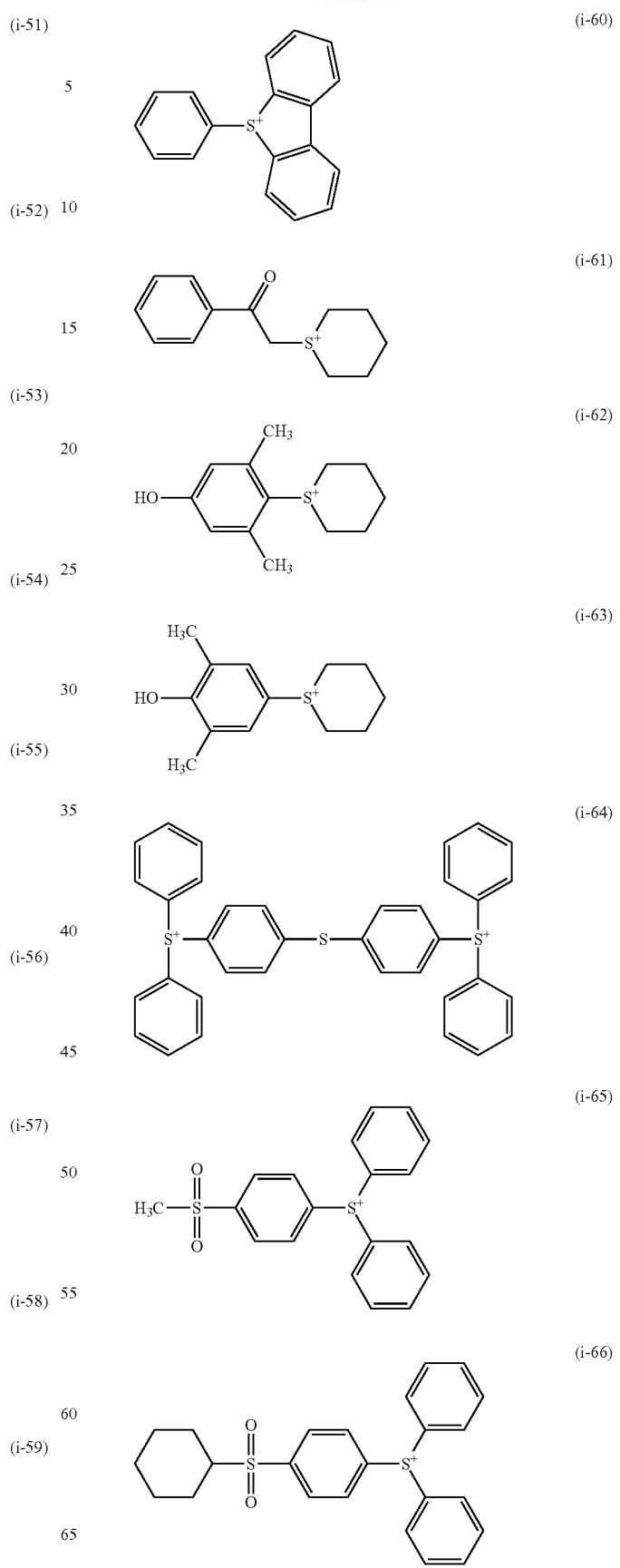

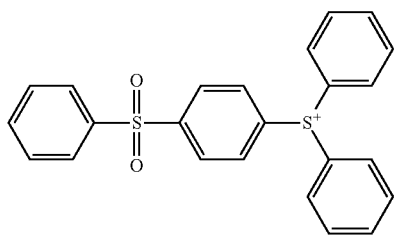

(i-67)

Among these preferred sulfonium cations, sulfonium cations represented by the above formula (i-1), formula (i-2), formula (i-6), formula (i-8), formula (i-13), formula (i-19), formula (i-25), formula (i-27), formula (i-29), formula (i-33), formula (i-51), formula (i-54), formula (i-55), formula (i-56) and formula (i-57) are more preferred.

Iodonium Cation

The iodonium cation is preferably an iodonium cation which is included in the compound (A) and is represented by the following formula (5a) or the following formula (5b), and the like. It is to be noted that the iodonium salts represented by the following formulae (5a) and (5b) are preferred compounds as the compound (A) in the embodiment of the present invention.

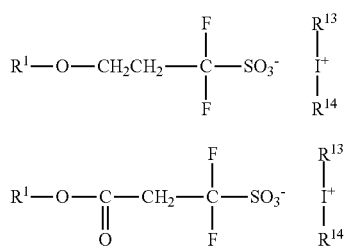

In the above formula, $R^1$ is as defined in the above formula (1); $R^{13}$ and $R^{14}$ each independently represent a linear or branched alkyl group having 1 to 10 carbon atoms, an alkenyl group having 1 to 10 carbon atoms, an oxoalkyl group having 1 to 10 carbon atoms, an aryl group having 6 to 18 carbon atoms, an aralkyl group having 6 to 18 carbon atoms or an aryloxoalkyl group having 6 to 18 carbon atoms, and optionally $R^{13}$ and $R^{14}$ bond to one another to taken together represent a ring together with the iodine atom in the formula, wherein a part or all of hydrogen atoms included in the alkyl group, the alkenyl group, the oxoalkyl group, the aryl group, the aralkyl group and the aryloxoalkyl group are not substituted or substituted.

An iodonium cation included in the iodonium salt represented by the above formulae (5a) and (5b) is preferably represented by the following formula (5-1).

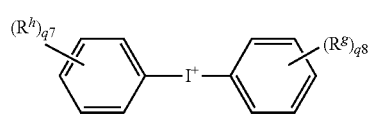

In the above formula (5-1), $R^h$ and $R^g$ each independently represent a hydrogen atom, a halogen atom, a linear or branched alkyl group having 1 to 12 carbon atoms, an alkoxy group having 1 to 12 carbon atoms, an aryl group having 6 to 12 carbon atoms, nitro group, or a group derived by combining any of these groups with at least one group selected from the group consisting of —COO—, —OCO—, —O— and —CO—, wherein a part or all of hydrogen atoms included in the alkyl group, the alkoxy group and the aryl group are not substituted or substituted; and q7 and q8 are each independently an integer of 0 to 5, wherein in the case where q7 and q8 are each 2 or greater, a plurality of $R^h$s are each identical or different and plurality of $R^g$s are each identical or different, and optionally any of a plurality of $R^f$s bond to one another to taken together represent a ring and any of a plurality of $R^g$s bond to one another to taken together represent a ring.

Of these, iodonium cations represented by the following formulae (ii-1) to (ii-39) are preferred.

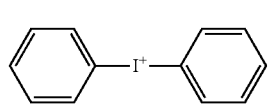

(ii-1)

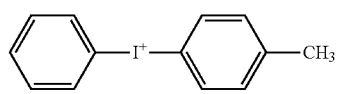

(ii-2)

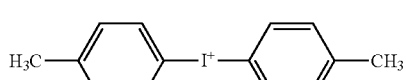

(ii-3)

(ii-4)

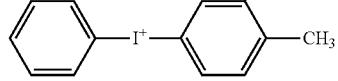

(ii-5)

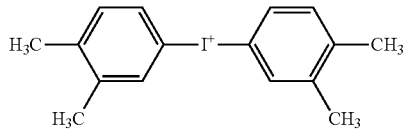

(ii-6)

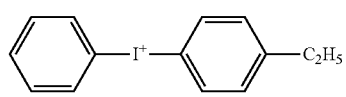

(ii-7)

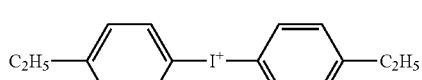

(ii-8)

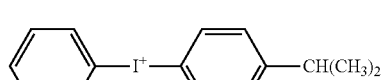

(ii-9)

(ii-10)

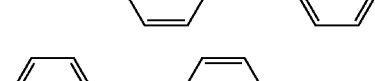

(ii-11)

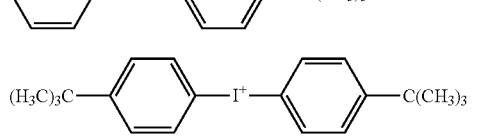

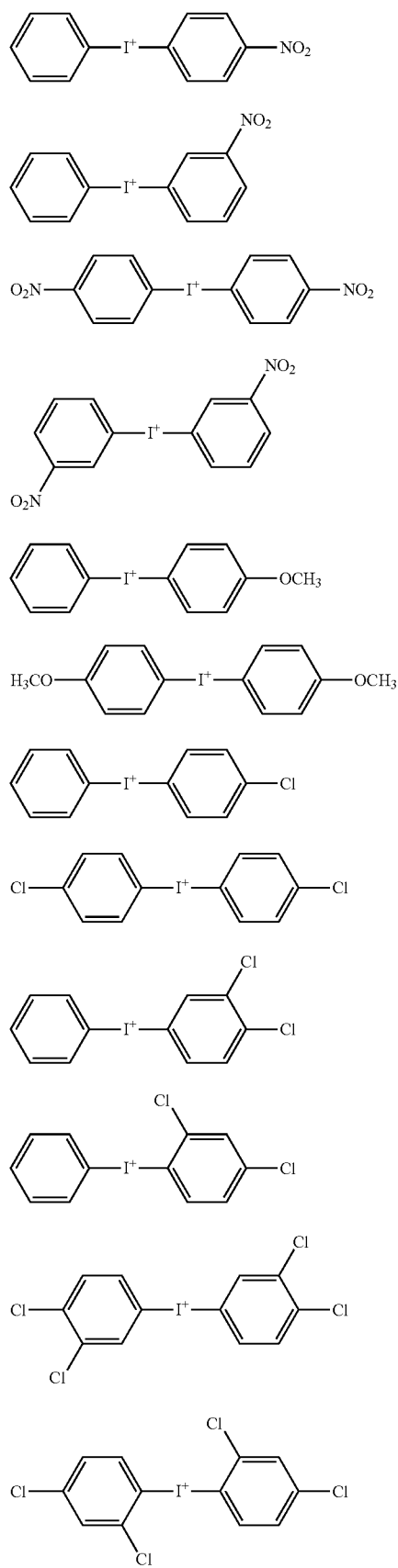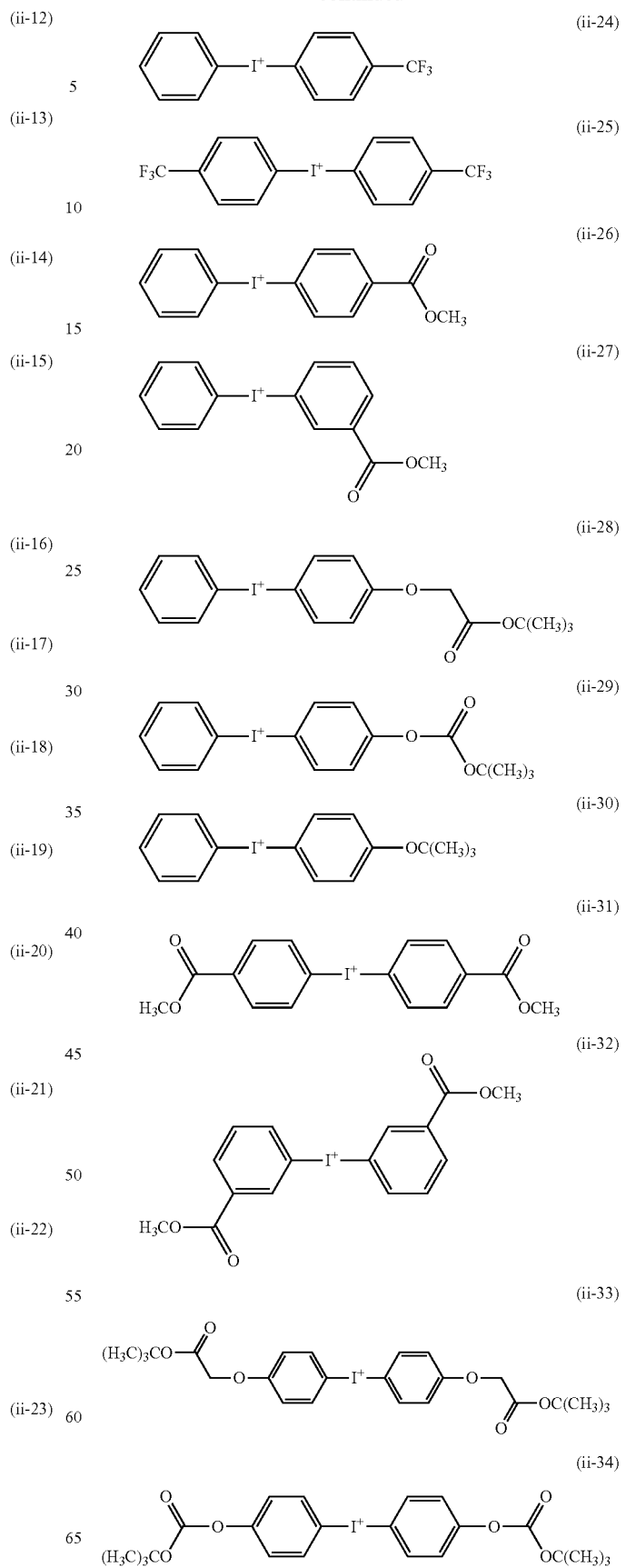

Among these, iodonium cations represented by the above formulae (ii-1) and (ii-11) are more preferred.

Preferred structures of the compound (A) are shown below.

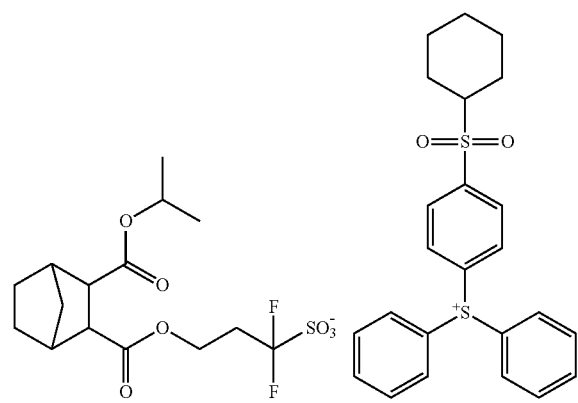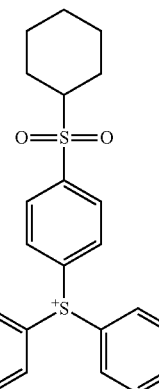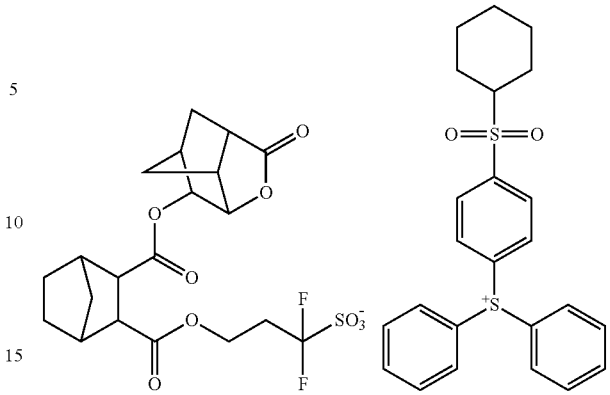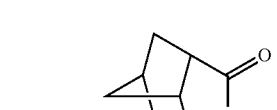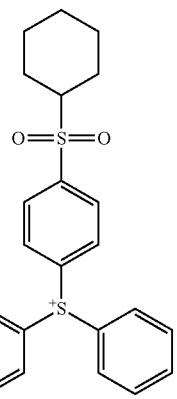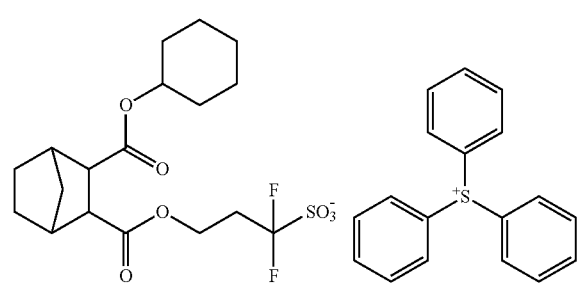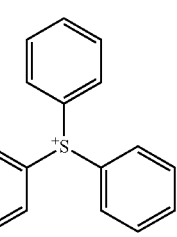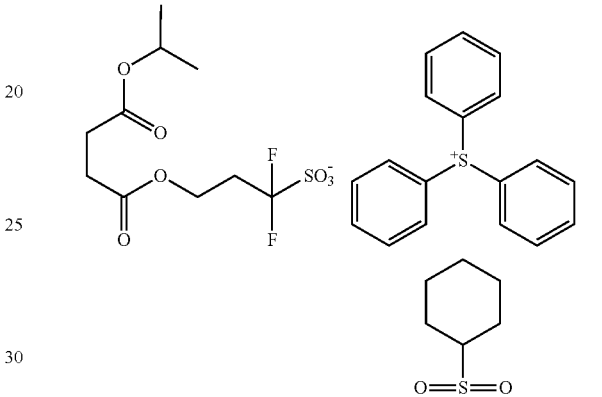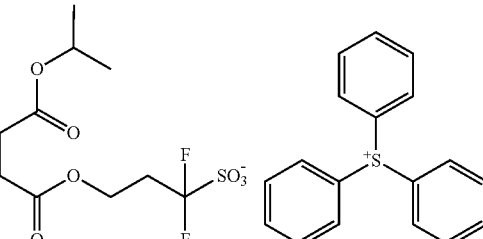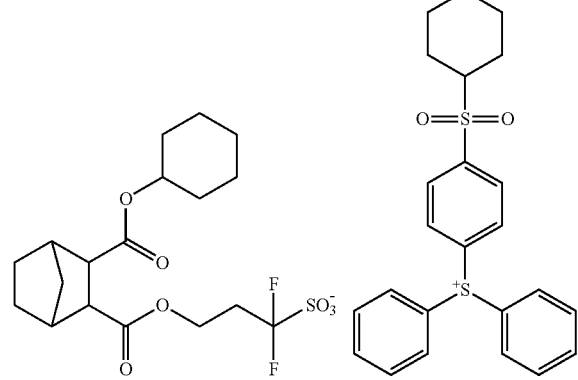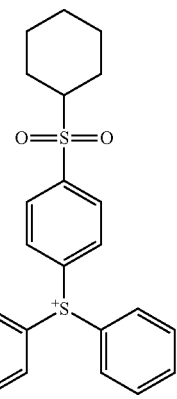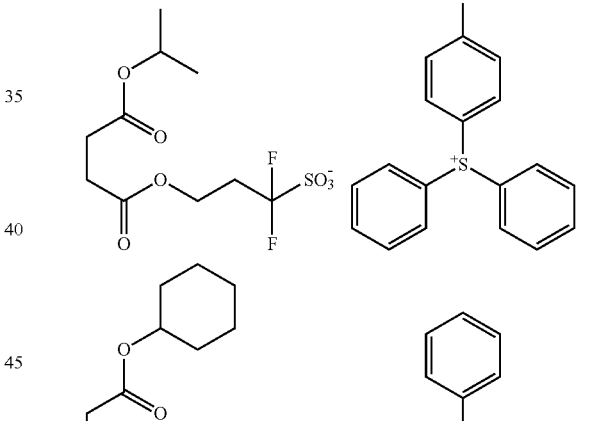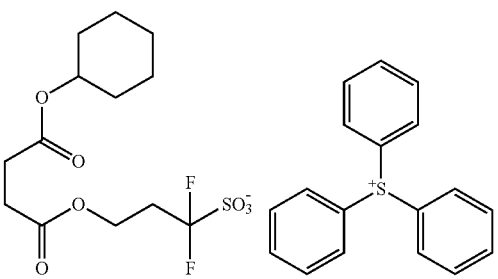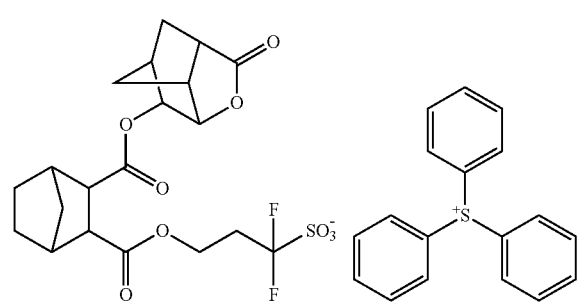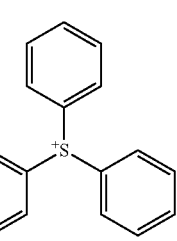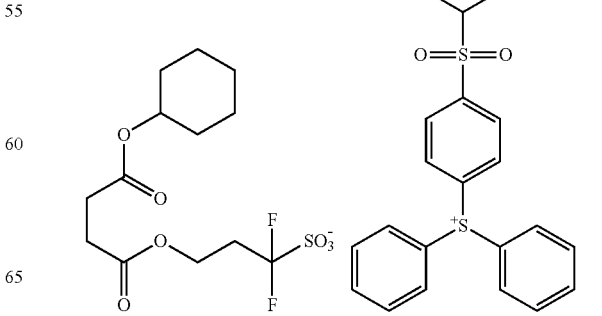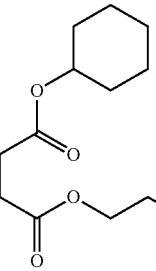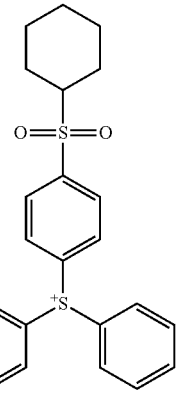

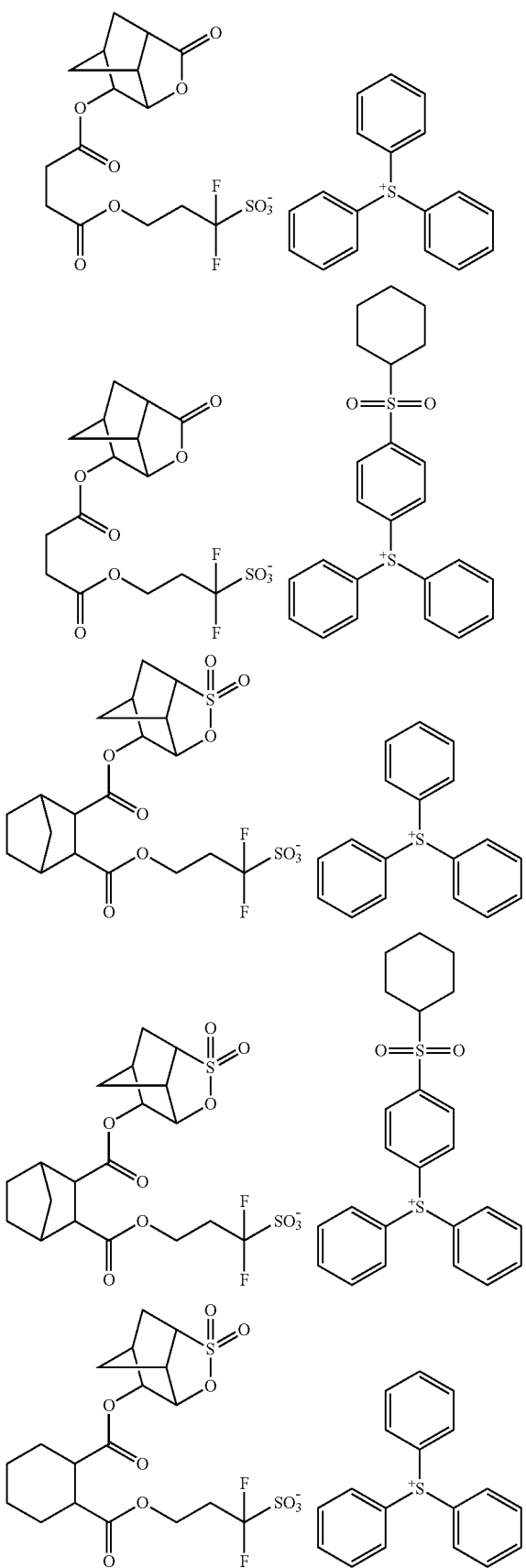
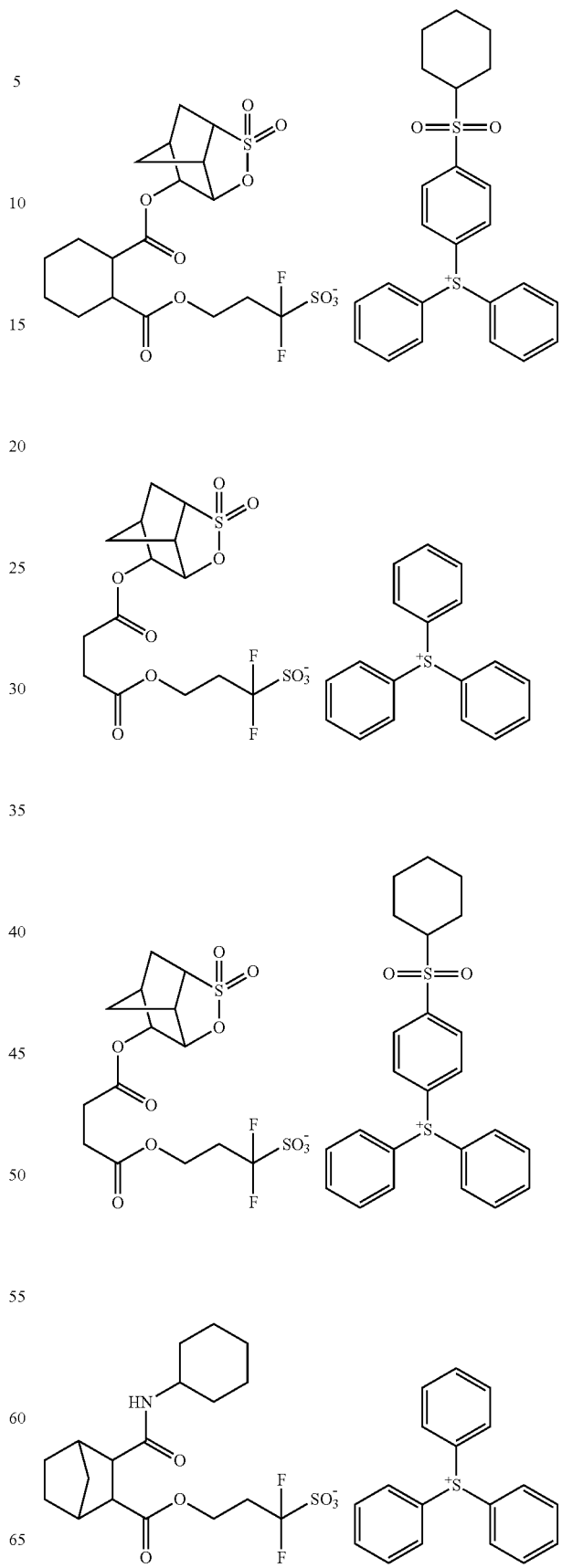

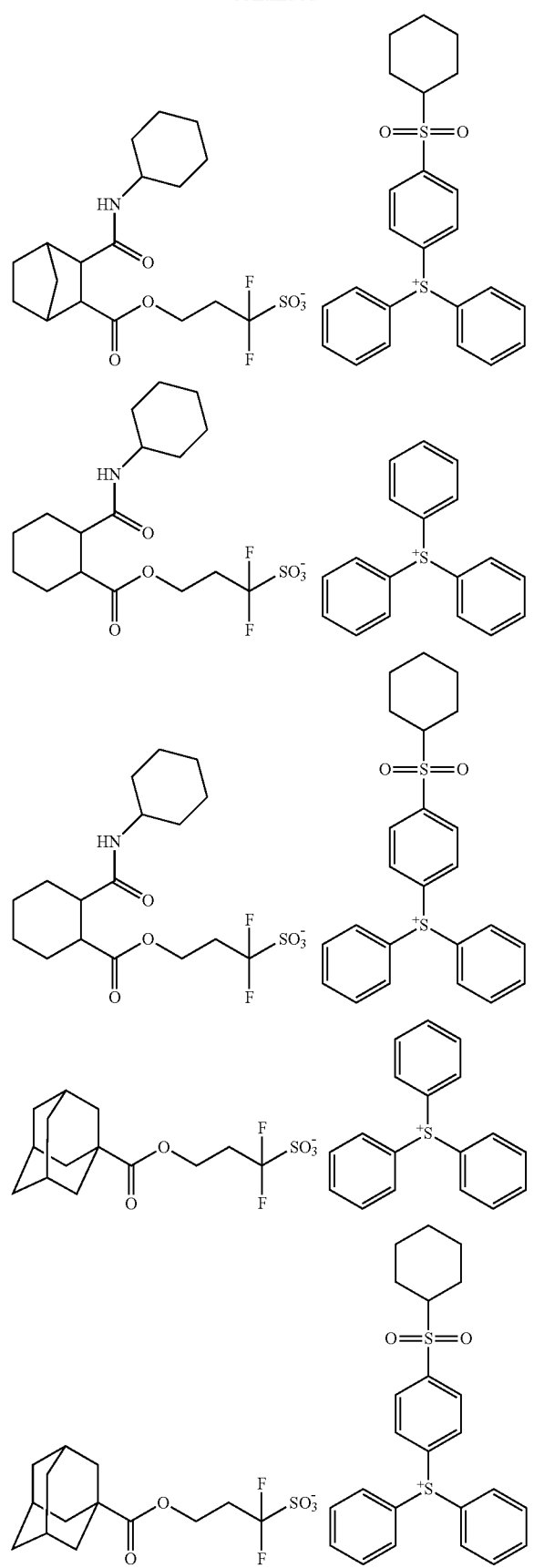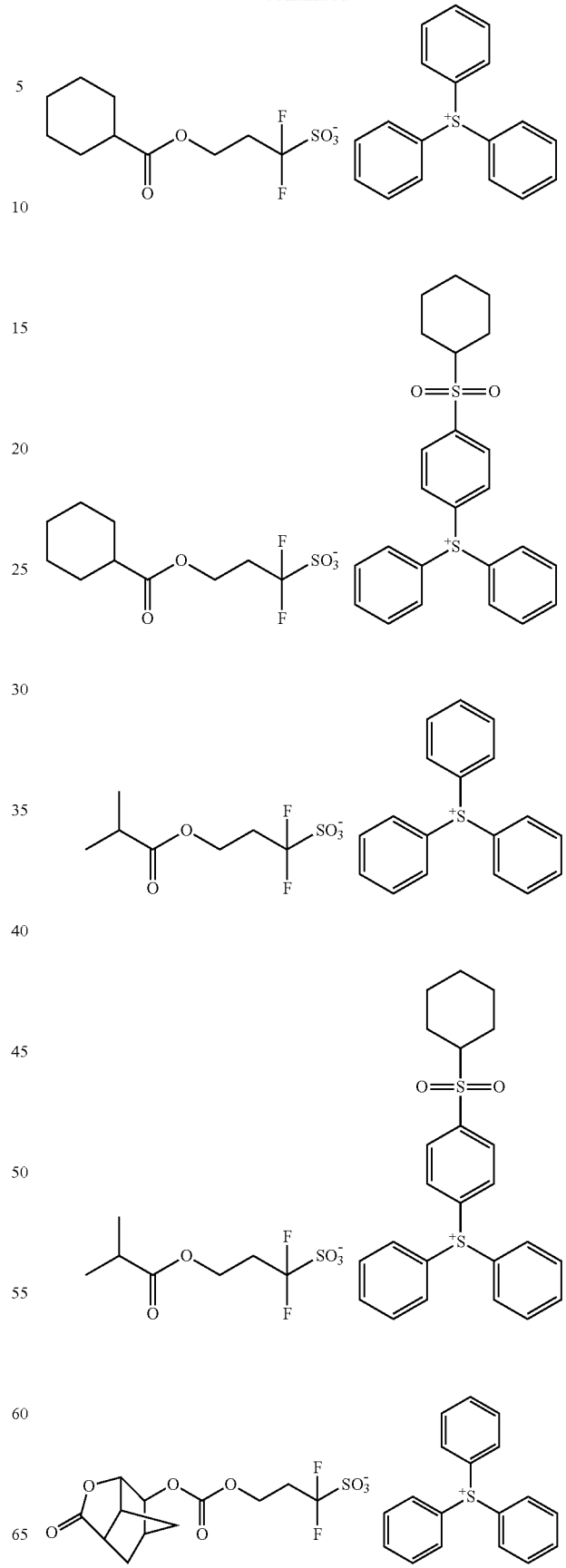

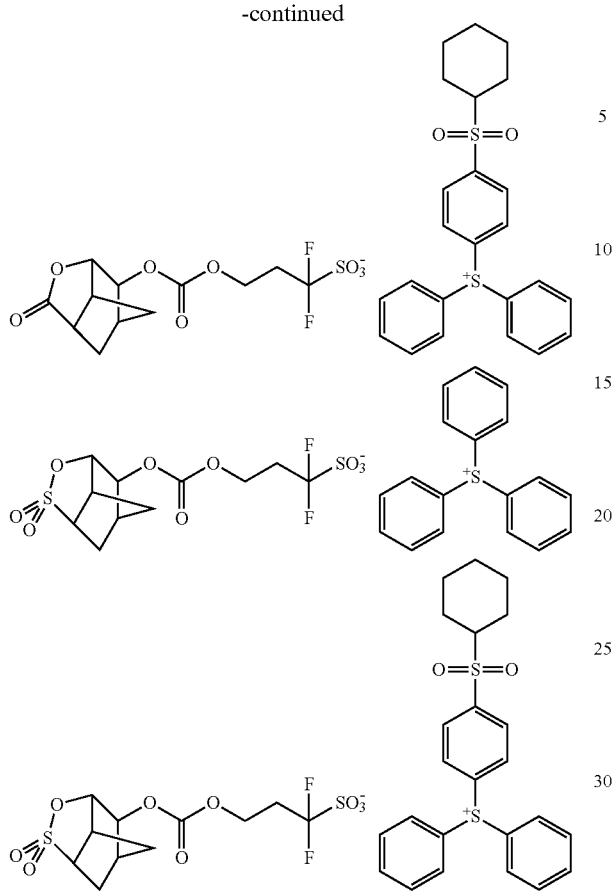

In the radiation-sensitive resin composition, the compound (A) may be used either alone or as a mixture of two or more thereof.

The amount of the compound (A) used in the radiation-sensitive resin composition may vary depending on the type of the compound (A), as well as the type of other radiation-sensitive compound described later which may be used as needed and the like, and is typically 0.1 to 40 parts by mass, preferably 5 to 40 parts by mass, and more preferably 5 to 35 parts by mass with respect to 100 parts by mass of the base polymer (B) described later. When the amount of the compound (A) used falls within the above-specified range, the radiation-sensitive resin composition achieves superior transparency to radioactive rays, pattern configuration, heat resistance, etc.

Synthesis Method of Compound (A)

The compound (A) may be synthesized by, for example, using a compound represented by the following formula (1-0) as a starting material, but the synthesis method is not limited thereto.

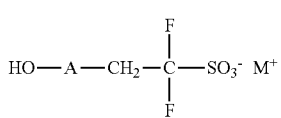

(1-0)

In the above formula (1-0), A and $M^+$ are as defined in the above formula (1).

The compound may be synthesized, for example, according to a method disclosed in Japanese Unexamined Patent Application, Publication No. 2008-007410 or Japanese Unexamined Patent Application, Publication No. 2008-007409 using 3-bromo-3,3-difluoropropanoic acid as a starting substance. The compound represented by the above formula (1) may be obtained according to a conventional procedure using the compound represented by the above formula (1-0) by way of, for example, a reaction presented in the following reaction formula.

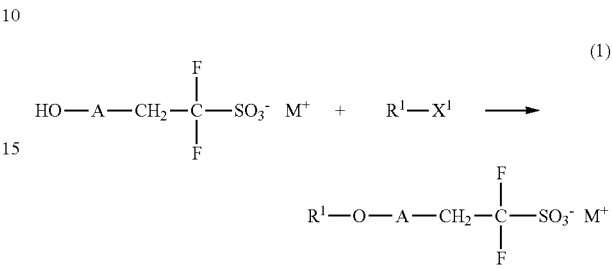

In the reaction formula, $R^1$, A and $M^+$ are as defined in the above formula (1); and $X^1$ represents a hydroxyl group or a halogen atom.

As an alternative to the method described above, the compound (A) may be obtained by way of a reaction presented in the following reaction formula.

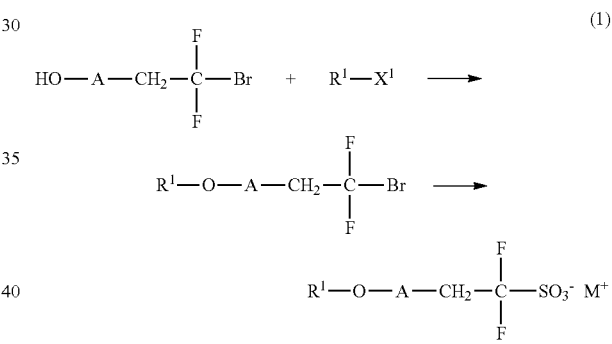

In the above reaction formula, $R^1$, A and $M^+$ are as defined in the above formula (1); and $X^1$ represents a hydroxyl group or a halogen atom.

In the radiation-sensitive resin composition, at least one compound other than the compound (A) (hereinafter, may be referred to as "other radiation-sensitive compound") may be used in combination as a radiation-sensitive acid generating agent.

Examples of the other radiation-sensitive compound include onium salt compounds, sulfone compounds, sulfonic acid esterified products, sulfonimide compounds, diazomethane compounds, disulfonylmethane compounds, oximesulfonate compounds, hydrazine sulfonate compounds, and the like.

These compounds are exemplified by compounds described in WO 2009/051088, paragraph nos. [0086] to [0113].

Of these other radiation-sensitive compounds, one, or two or more compounds selected from the group consisting of an onium salt compound, a sulfonimide compound and a diazomethane compound are preferably used.

Examples of particularly preferred other radiation-sensitive compound include diphenyliodonium trifluoromethanesulfonate, diphenyliodonium nonafluoro-n-butanesulfonate, diphenyliodonium p-toluenesulfonate, diphenyliodonium 10-camphorsulfonate, diphenyliodonium 2-trifluoromethylbenzenesulfonate, diphenyliodonium 4-trifluoromethylbenzenesulfonate, diphenyliodonium 2,4-difluorobenzenesulfonate, diphenyliodonium 1,1,2,2-tetrafluoro-2-(norbornan-2-yl)ethanesulfonate, diphenyliodonium 2-(5-t-butoxycarbonyloxybicyclo[2.2.1]heptan-2-yl)-1,1,2,2-tetrafluoroethanesulfonate, diphenyliodonium 2-(6-t-butoxycarbonyloxybicyclo[2.2.1]heptan-2-yl)-1,1,2,2-tetrafluoroethanesulfonate, diphenyliodonium 1,1-difluoro-2-(bicyclo[2.2.1]heptan-2-yl)ethanesulfonate, bis(4-t-butylphenyl)iodonium trifluoromethanesulfonate, bis(4-t-butylphenyl)iodonium nonafluoro-n-butanesulfonate, bis(4-t-butylphenyl)iodonium p-toluenesulfonate, bis(4-t-butylphenyl)iodonium 10-camphorsulfonate, bis(4-t-butylphenyl)iodonium 2-trifluoromethylbenzenesulfonate, bis(4-t-butylphenyl)iodonium 4-trifluoromethylbenzenesulfonate, bis(4-t-butylphenyl)iodonium 2,4-difluorobenzenesulfonate, bis(4-t-butylphenyl)iodonium 1,1,2,2-tetrafluoro-2-(norbornan-2-yl)ethanesulfonate, bis(4-t-butylphenyl)iodonium 1,1-difluoro-2-(bicyclo[2.2.1]heptan-2-yl)ethanesulfonate, triphenylsulfonium trifluoromethanesulfonate, triphenylsulfonium nonafluoro-n-butanesulfonate, triphenylsulfonium p-toluenesulfonate, triphenylsulfonium 10-camphorsulfonate, triphenylsulfonium 2-trifluoromethylbenzenesulfonate, triphenylsulfonium 4-trifluoromethylbenzenesulfonate, triphenylsulfonium 2,4-difluorobenzenesulfonate, triphenylsulfonium 1,1,2,2-tetrafluoro-2-(norbornan-2-yl)ethanesulfonate, triphenylsulfonium 2-(5-t-butoxycarbonyloxybicyclo[2.2.1]heptan-2-yl)-1,1,2,2-tetrafluoroethanesulfonate, triphenylsulfonium 2-(6-t-butoxycarbonyloxybicyclo[2.2.1]heptan-2-yl)-1,1,2,2-tetrafluoroethanesulfonate, triphenylsulfonium 2-(5-pivaloyloxybicyclo[2.2.1]heptan-2-yl)-1,1,2,2-tetrafluoroethanesulfonate, triphenylsulfonium 2-(6-pivaloyloxybicyclo[2.2.1]heptan-2-yl)-1,1,2,2-tetrafluoroethanesulfonate, triphenylsulfonium 2-(5-hydroxybicyclo[2.2.1]heptan-2-yl)-1,1,2,2-tetrafluoroethanesulfonate, triphenylsulfonium 2-(6-hydroxybicyclo[2.2.1]heptan-2-yl)-1,1,2,2-tetrafluoroethanesulfonate, triphenylsulfonium 2-(5-methanesulfonyloxybicyclo[2.2.1]heptan-2-yl)-1,1,2,2-tetrafluoroethanesulfonate, triphenylsulfonium 2-(6-methanesulfonyloxybicyclo[2.2.1]heptan-2-yl)-1,1,2,2-tetrafluoroethanesulfonate, triphenylsulfonium 2-(5-i-propanesulfonyloxybicyclo[2.2.1]heptan-2-yl)-1,1,2,2-tetrafluoroethanesulfonate, triphenylsulfonium 2-(6-i-propanesulfonyloxybicyclo[2.2.1]heptan-2-yl)-1,1,2,2-tetrafluoroethanesulfonate, triphenylsulfonium 2-(5-n-hexanesulfonyloxybicyclo[2.2.1]heptan-2-yl)-1,1,2,2-tetrafluoroethanesulfonate, triphenylsulfonium 2-(6-n-hexanesulfonyloxybicyclo[2.2.1]heptan-2-yl)-1,1,2,2-tetrafluoroethanesulfonate, triphenylsulfonium 2-(5-oxobicyclo[2.2.1]heptan-2-yl)-1,1,2,2-tetrafluoroethanesulfonate, triphenylsulfonium 2-(6-oxobicyclo[2.2.1]heptan-2-yl)-1,1,2,2-tetrafluoroethanesulfonate, triphenylsulfonium 1,1-difluoro-2-(bicyclo[2.2.1]heptan-2-yl)ethanesulfonate, 1-(4-n-butoxynaphthalen-1-yl)tetrahydrothiophenium trifluoromethanesulfonate, 1-(4-n-butoxynaphthalen-1-yl)tetrahydrothiophenium nonafluoro-n-butanesulfonate, 1-(4-n-butoxynaphthalen-1-yl)tetrahydrothiophenium 1,1,2,2-tetrafluoro-2-(norbornan-2-yl)ethanesulfonate, 1-(4-n-butoxynaphthalen-1-yl)tetrahydrothiophenium 2-(5-t-butoxycarbonyloxybicyclo[2.2.1]heptan-2-yl)-1,1,2,2-tetrafluoroethanesulfonate, 1-(4-n-butoxynaphthalen-1-yl)tetrahydrothiophenium 2-(6-t-butoxycarbonyloxybicyclo[2.2.1]heptan-2-yl)-1,1,2,2-tetrafluoroethanesulfonate, 1-(4-n-butoxynaphthalen-1-yl)tetrahydrothiophenium 1,1-difluoro-2-(bicyclo[2.2.1]heptan-2-yl)ethanesulfonate, N-(trifluoromethanesulfonyloxy)succinimide, N-(10-camphorsulfonyloxy)succinimide, N-[(5-methyl-5-carboxymethylbicyclo[2.2.1]heptan-2-yl)sulfonyloxy]succinimide, N-(trifluoromethanesulfonyloxy)bicyclo[2.2.1]hept-5-ene-2,3-dicarboxylmide, N-(nonafluoro-n-butanesulfonyloxy)bicyclo[2.2.1]hept-5-ene-2,3-dicarboxylmide, N-[1,1,2,2-tetrafluoro-2-(norbornan-2-yl)ethanesulfonyloxy]bicyclo[2.2.1]hept-5-ene-2,3-dicarboxylmide, N-(10-camphorsulfonyloxy)bicyclo[2.2.1]hept-5-ene-2,3-dicarboxylmide, N-[2-(5-oxobicyclo[2.2.1]heptan-2-yl)-1,1,2,2-tetrafluoroethanesulfonyloxy]bicyclo[2.2.1]hept-5-ene-2,3-dicarboxylmide, N-[2-(6-oxobicyclo[2.2.1]heptan-2-yl)-1,1,2,2-tetrafluoroethanesulfonyloxy]bicyclo[2.2.1]hept-5-ene-2,3-dicarboxylmide, N-[1,1-difluoro-2-(bicyclo[2.2.1]heptan-2-yl)ethanesulfonyloxy]bicyclo[2.2.1]hept-5-ene-2,3-dicarboxylmide, bis(cyclohexanesulfonyl)diazomethane, bis(t-butylsulfonyl)diazomethane, bis(1,4-dioxaspiro[4.5]decane-7-sulfonyl)diazomethane, and the like.

The proportion of the other radiation-sensitive compound used may be appropriately selected in accordance with the type of the other radiation-sensitive compound, etc., and is typically no greater than 95 parts by mass, preferably no greater than 90 parts by mass, and more preferably no greater than 80 parts by mass with respect to 100 parts by mass of the total of the compound (A) and the other radiation-sensitive compound. In this case, when the proportion of the other radiation-sensitive compound used is excessive, desired effects of the present invention may be impaired.

(B) Base Polymer

The base polymer (B) of the embodiment of the present invention is a polymer that is a principal component of polymers included in the radiation-sensitive resin composition, and is contained at a greatest content. Exemplary preferred polymers as such a base polymer may include: a polymer which is insoluble or hardly soluble in alkali and has an acid-labile group and which becomes easily soluble in alkali when the acid-labile group is dissociated (hereinafter, may be also referred to as "acid-labile group-containing polymer (B1)"); a polymer that is soluble in an alkaline developer solution and has one or more types of functional group, e.g., an oxygen-containing functional group such as a phenolic hydroxyl group, an alcoholic hydroxyl group and a carboxyl group, which exhibits affinity to the alkaline developer solution (hereinafter, may be also referred to as "alkali-soluble polymer (B2)"). The radiation-sensitive resin composition which contains the acid-labile group-containing polymer (B1) can be suitably used as a positive type radiation-sensitive resin composition, whereas the radiation-sensitive resin composition containing the alkali-soluble polymer (B2) can be suitably used as a negative radiation-sensitive resin composition. The acid-labile group-containing polymer (B1) and the alkali-soluble polymer (B2) will be described in detail below.

The term "insoluble or hardly soluble in alkali" as referred to herein means a property that no less than 50% of the initial film thickness of a film remains after development in the case where the film formed using only the polymer containing an acid-labile group is developed in place of the resist film under alkali development conditions employed in forming a resist pattern from a resist film formed using a radiation-sensitive resin composition that contains the polymer containing an acid-labile group.

Proportion of Fluorine Atom Contained

When used together with the fluorine atom-containing polymer (C) described later, the proportion of the fluorine atom contained in the base polymer (B) is typically less than 5% by mass, preferably 0 to 4.9% by mass, and more preferably 0 to 4% by mass with respect to 100% by mass of the entirety of the fluorine-containing polymer (C). It is to be noted that the proportion of the fluorine atom contained may be determined by $^{13}$C-NMR.

(B1) Acid-Labile Group-Containing Polymer

The acid-labile group in the acid-labile group-containing polymer (B1) means, for example, a group that is derived by substituting hydrogen atoms in an acidic functional group such as a phenolic hydroxyl group, a carboxyl group or a sulfonic acid group, and is dissociated in the presence of an acid. Such an acid-labile group is exemplified by a substituted methyl group, a 1-substituted ethyl group, a 1-substituted-n-propyl group, a 1-branched alkyl group, an alkoxycarbonyl group, an acyl group, a cyclic acid-labile group, and the like.

Examples of the substituted methyl group may include those disclosed in WO 2009/051088, paragraph [0117]. Examples of the 1-substituted ethyl group may include those disclosed in WO 2009/051088, paragraph [0118]. Examples of the 1-substituted-n-propyl group may include those disclosed in WO 2009/051088, paragraph [0119]. Examples of the acyl group may include those disclosed in WO 2009/051088, paragraph [0120]. Furthermore, examples of the cyclic acid-labile group may include those disclosed in WO 2009/051088, paragraph [0121].

Among these acid-labile groups, a benzyl group, a t-butoxycarbonylmethyl group, a 1-methoxyethyl group, a 1-ethoxyethyl group, a 1-cyclohexyloxyethyl group, a 1-ethoxy-n-propyl group, a t-butyl group, a 1,1-dimethylpropyl group, a t-butoxycarbonyl group, a tetrahydropyranyl group, a tetrahydrofuranyl group, a tetrahydrothiopyranyl group, a tetrahydrothiofuranyl group and the like are preferred. In the acid-labile group-containing polymer (B1), one or more types of the acid-labile group may be included.

The percentage introduction of the acid-labile group in the acid-labile group-containing polymer (B1), i.e., a rate of the number of acid-labile groups to the total number of acidic functional groups and the acid-labile groups in the acid-labile group-containing polymer (B1), may be appropriately selected depending on the type of the acid-labile group and the polymer into which the group is introduced, and is preferably 5 to 100% and more preferably 10 to 100%.

The structure of the acid-labile group-containing polymer (B1) is not particularly limited as long as the properties described above are provided, and a variety of structures are acceptable. However, the acid-labile group-containing polymer (B1) is particularly preferably a polymer derived by substituting a part or all of hydrogen atoms of a phenolic hydroxyl group in poly(4-hydroxystyrene) with an acid-labile group, or a polymer derived by substituting with an acid-labile group a part or all hydrogen atoms of phenolic hydroxyl group and/or hydrogen atoms of carboxyl group in a copolymer of 4-hydroxystyrene and/or 4-hydroxy-α-methylstyrene with (meth)acrylic acid, or the like.

The structure of the acid-labile group-containing polymer (B1) may be appropriately selected depending on the type of the radioactive ray employed. For example, in a radiation-sensitive positive type resin composition for which KrF excimer laser is used, a particularly suitable acid-labile group-containing polymer (B1) is preferably, for example, a polymer that is insoluble or hardly soluble in alkali having a structure unit represented by the following formula (4) (hereinafter, may be also referred to as "structure unit (4)"), and a structure unit provided by protecting a phenolic hydroxyl group in the structure unit (4) with the acid-labile group. It is to be noted that the acid-labile group-containing polymer (B1) may be also suitably used in a positive type radiation-sensitive resin composition for which other radioactive rays such as an ArF excimer laser, an F2 excimer laser and an electron beam are employed.

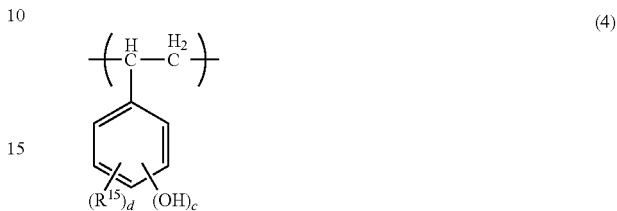

In the above formula (4), $R^{15}$ represents a hydrogen atom or a monovalent organic group; and c and d are each independently represent an integer of 1 to 3, wherein in the case where d is 2 or greater, a plurality of $R^{15}$s are each identical or different.

The structural unit (4) is particularly preferably a structural unit derived by cleavage of a nonaromatic double bond of 4-hydroxystyrene. In addition, the acid-labile group-containing polymer (B1) may further include other structural unit.

Examples of the other structural unit include units derived by cleaving a polymerizable unsaturated bond of a vinylaromatic compound such as styrene or α-methylstyrene; a (meth)ester acrylate such as t-butyl(meth)acrylate, adamantyl(meth)acrylate or, 2-methyladamantyl(meth)acrylate, an the like.

The acid-labile group-containing polymer (B1) particularly suited in a positive type radiation-sensitive resin composition for which an ArF excimer laser is employed is preferably a polymer that is insoluble or hardly soluble in alkali, having the structural unit represented by the above formula (2) (hereinafter, may be also referred to as "structural unit (2)"). It is to be noted that this polymer may be suitably used in a positive type radiation-sensitive resin composition for which other radioactive ray such as a KrF excimer laser, an F2 excimer laser or an electron beam is employed.

In the above formula (2), $R^6$ represents a hydrogen atom or a methyl group; $R^7$ represents a linear or branched alkyl group having 1 to 4 carbon atoms, or an alicyclic hydrocarbon group having 4 to 20 carbon atoms; and $R^8$ and $R^9$ each independently represent a linear or branched alkyl group having 1 to 4 carbon atoms, or an alicyclic hydrocarbon group having 4 to 20 carbon atoms, or $R^8$ and $R^9$ bond to one another to taken together represent an alicyclic hydrocarbon group having 4 to 20 carbon atoms together with the carbon atom to which $R^8$ and $R^9$ bond.

Examples of the linear or branched alkyl group having 1 to 4 carbon atoms which may be represented by $R^7$ to $R^9$ include a methyl group, an ethyl group, a n-propyl group, a n-butyl group, and the like.

Examples of the alicyclic hydrocarbon group having 4 to 20 carbon atoms which may be represented by $R^7$ to $R^9$, and the alicyclic hydrocarbon group having 4 to 20 carbon atoms taken together represented by $R^8$ and $R^9$ bonded to one another together with the carbon atom to which $R^8$ and $R^9$ bond include a cyclobutyl group, a cyclopentyl group, a cyclohexyl group, a norbornyl group, an adamantyl group, and the like.

The structural unit (2) is preferably represented by the following formulae (2-1) to (2-18), and of these, structural units represented by the following formulae (2-3), (2-4), (2-9), (2-12) and (2-13) are more preferred. The acid-labile group-containing polymer (B1) may include either one type alone, or two or more types of the structural unit (2).
(2-1)
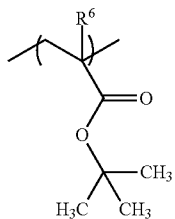
(2-2)
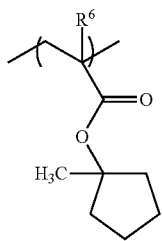
(2-3)
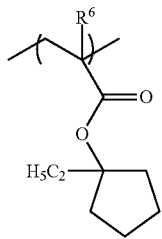
(2-4)
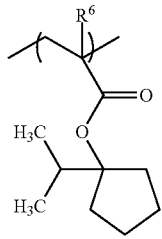
(2-5)
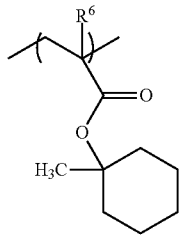
(2-6)
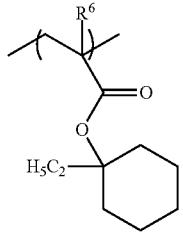
(2-7)
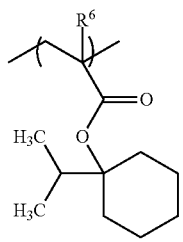
(2-8)
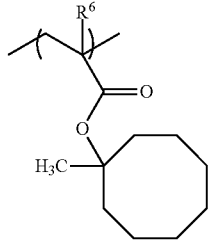
(2-9)
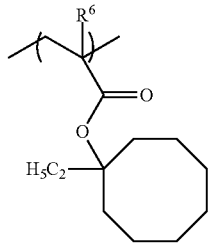
(2-10)
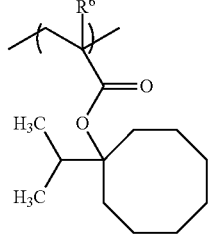
(2-11)
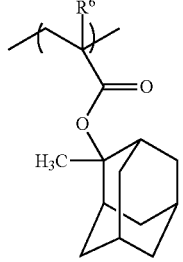
(2-12)
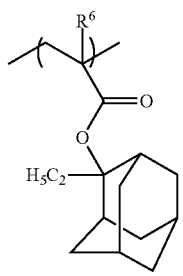

(2-13) 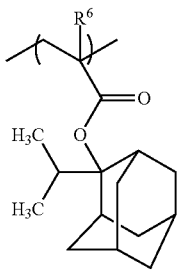
(2-14) 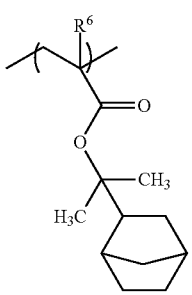
(2-15) 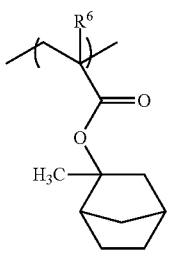
(2-16) 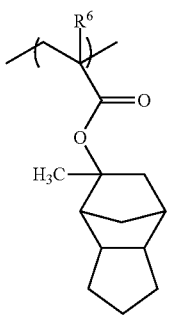
(2-17) 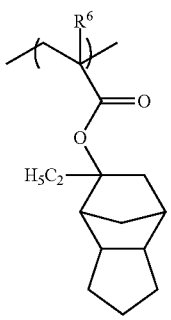
(2-18) 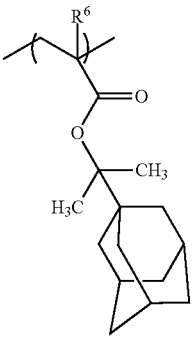
In the above formula, $R^6$ is as defined in the above formula (2).
The acid-labile group-containing polymer (B1) preferably includes one or more types of structural unit having a lactone skeleton or a cyclic carbonate skeleton represented by the following formulae (hereinafter, may be also referred to as "structural unit (3)").
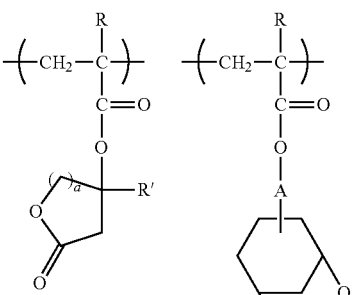
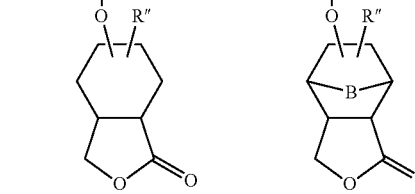
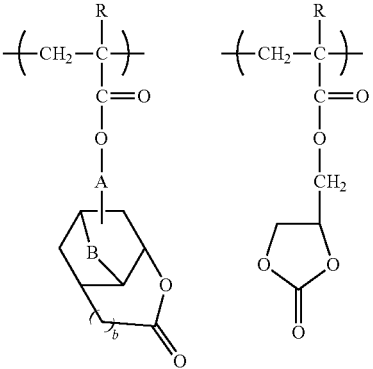

In the above formula, R and R' each independently represent a hydrogen atom or a methyl group; R" represents a hydrogen atom or a methoxy group; A represents a single bond or a methylene group; B represents a methylene group or an oxygen atom; and a and b are 0 or 1.

The structural unit (3) is particularly preferably a structural unit represented by the following formulae. It is to be noted that in the following formulae, R each independently represents a hydrogen atom or a methyl group.

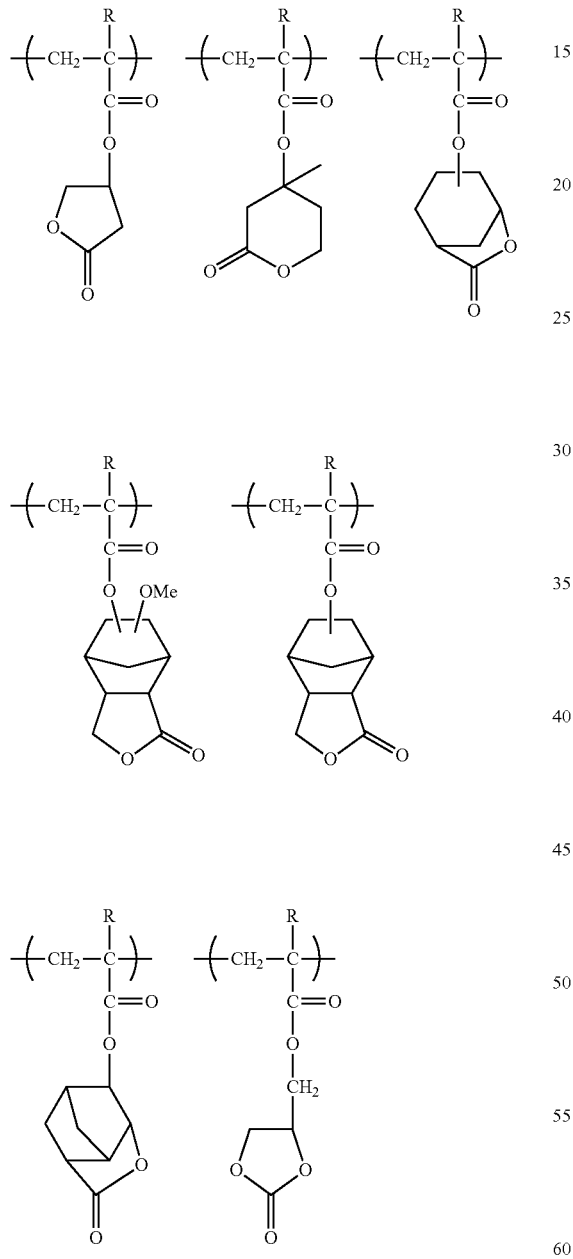

The acid-labile group-containing polymer (B1) may include a structural unit having a functional group represented by the following formulae. It is to be noted that in the following formulae, R each independently represents a hydrogen atom or a methyl group.

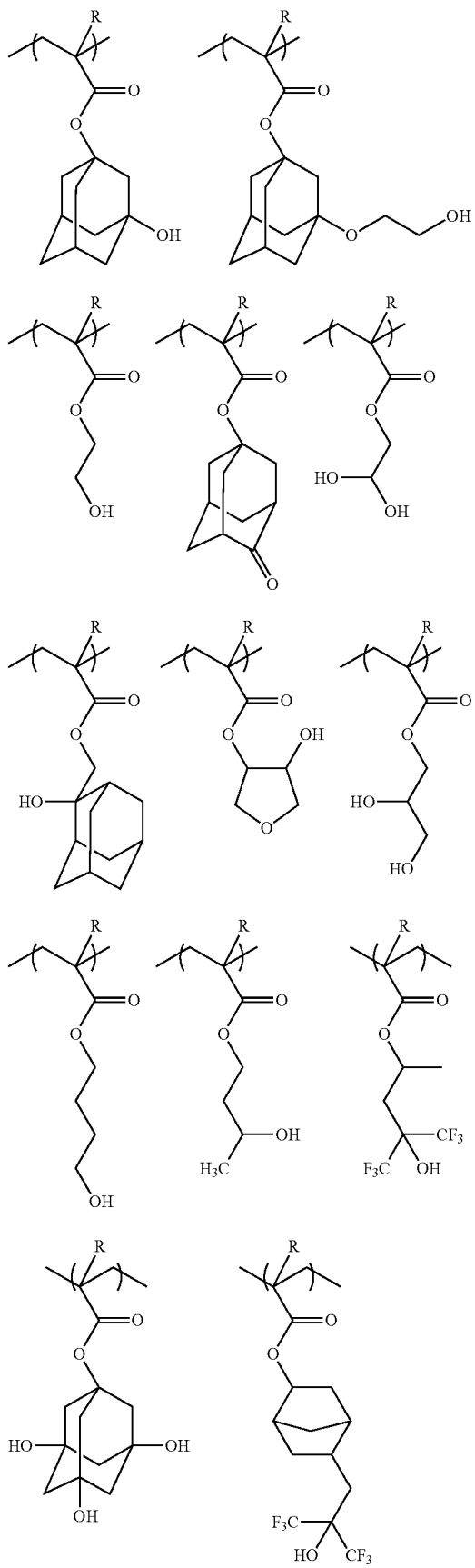

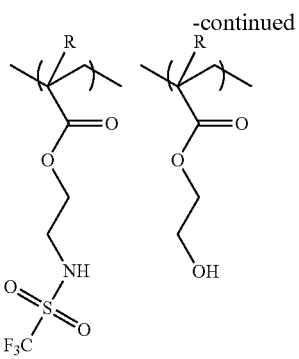

The acid-labile group-containing polymer (B1) may include a structural unit derived from alkyl(meth)acrylate such as methyl(meth)acrylate, ethyl(meth)acrylate, butyl (meth)acrylate, lauryl(meth)acrylate, cyclohexyl(meth)acrylate, (meth)acrylic acid-bicyclo[2.2.1]heptyl ester, (meth)acrylic acid-cyclohexyl ester, (meth)acrylic acid-bicyclo[4.4.0]decanyl ester, (meth)acrylic acid-bicyclo[2.2.2]octyl ester, (meth)acrylic acid-tricyclo[5.2.1.0$^{2,6}$]decanyl ester, (meth)acrylic acid-adamantyl and (meth)acrylic acid-tricyclo[3.3.1.1$^{3,7}$]decanyl ester.

The acid-labile group-containing polymer (B1) which may be particularly suitably used in a positive type radiation-sensitive resin composition for which an F2 excimer laser is employed is exemplified by those described in WO 2009/051088, paragraphs [0136] to [0147].

In the case in which the acid-labile group-containing polymer (B1) is produced by polymerization of a polymerizable unsaturated monomer or through the aforementioned polymerization, a branched structure can be introduced into the acid-labile group-containing polymer (B1) by a unit derived from a polyfunctional monomer having two or more polymerizable unsaturated bonds, and/or an acetal type crosslinking group. The introduction of such a branched structure enables the heat resistance of the acid-labile group-containing polymer (B1) to be enhanced.

In this case, the percentage introduction of the branched structure in the acid-labile group-containing polymer (B1) may be appropriately selected depending on the type of the branched structure and the acid-labile group-containing polymer (B1) into which the structure is introduced, but is preferably no greater than 10 mol % with respect to all the structure units.

The molecular weight of the acid-labile group-containing polymer (B1) is not particularly limited and may be appropriately predetermined, but the polystyrene equivalent weight molecular weight (hereinafter, may be referred to as "Mw") as determined by gel permeation chromatography (GPC) is typically 1,000 to 500,000, preferably 2,000 to 400,000, and more preferably 3,000 to 300,000.

The Mw of the acid-labile group-containing polymer (B1) having no branched structure is preferably 1,000 to 150,000, and more preferably 3,000 to 100,000. The Mw of the acid-labile group-containing polymer (B1) having a branched structure is preferably 5,000 to 500,000, and more preferably 8,000 to 300,000. Use of the acid-labile group-containing polymer (B1) having the Mw falling within such a range makes the resultant resist film excellent in developability with alkali.

The ratio (Mw/Mn) of the Mw to the polystyrene equivalent number average molecular weight (hereinafter, may be referred to as "Mn") as determined by GPC, of the acid-labile group-containing polymer (B1) is also not particularly limited, and is typically 1 to 10, preferably 1 to 8, and more preferably 1 to 5. Use of the acid-labile group-containing polymer (B1) having the Mw/Mn falling within such a range makes the resultant resist excellent in resolving ability. In the radiation-sensitive resin composition of the embodiment of the present invention, the acid-labile group-containing polymer (B1) may be used either alone, or as a mixture of two or more thereof.

Although the method for producing the acid-labile group-containing polymer (B1) is not particularly limited, for example, the acid-labile group-containing polymer (B1) may be produced by: a method which includes introducing one or more types of acid-labile group into an acidic functional group in an alkali-soluble polymer produced beforehand; a method which includes polymerizing one or more types of polymerizable unsaturated monomer having an acid-labile group with one or more types of other polymerizable unsaturated monomer as the case may be; a method which includes the polycondensation of one or more types of polycondensible components having an acid-labile group with other polycondensible component as the case may be; or the like.

For the polymerization of the polymerizable unsaturated monomer in producing the alkali-soluble polymer, and for the polymerization of the polymerizable unsaturated monomer having an acid-labile group, a polymerization initiator such as a radical polymerization initiator, a polymerization catalyst such as an anion polymerization catalyst, a coordinated anion polymerization catalyst or a cation polymerization catalyst may be appropriately selected depending on the type of the polymerizable unsaturated monomer used and the reaction medium, etc., and the polymerization may be conducted in an appropriate polymerization system for block polymerization, solution polymerization, precipitation polymerization, emulsion polymerization, suspension polymerization, block-suspension polymerization or the like.

The polycondensation of the polycondensible component having an acid-labile group can be carried out preferably in the presence of an acidic catalyst, or in an aqueous medium or a mixed medium of water and a hydrophilic solvent.

(B2) Alkali-Soluble Polymer

The alkali-soluble polymer (B2) is exemplified by polymers that include at least one structural unit selected from the group consisting of a structural unit represented by the following formula (5) (hereinafter, may be referred to as "structural unit (5)"), a structural unit represented by the following formula (6) (hereinafter, may be referred to as "structural unit (6)") and a structural unit represented by the following formula (7) (hereinafter, may be referred to as "structural unit (7)"), and the like.

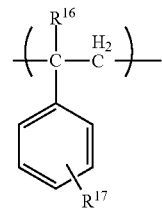

(5)

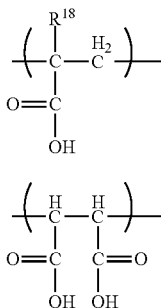

(6)

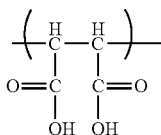

(7)

In the above formula (15) and in the formula (16), $R^{16}$ and $R^{18}$ each independently represent a hydrogen atom or a methyl group; $R^{17}$ represents a hydroxyl group, a carboxyl group, —$R^{19}$COOH, —O$R^{19}$COOH, —OCO$R^{19}$COOH or COO$R^{19}$COOH, wherein $R^{19}$ represents —$(CH_2)_e$—; and e is an integer of 1 to 4.

The alkali-soluble polymer (B2) may be constituted with the structural unit (5), the structural unit (6) or the structural unit (7) alone, but one or more types of other structural unit may be further included as long as the resultant polymer is soluble in alkaline developer solutions. The other structural unit is exemplified by structural units similar to the other structural unit in the acid-labile group-containing polymer (B1) described above, and the like.

The total content of the structural unit (5), the structural unit (6) and the structural unit (7) in the alkali-soluble polymer (B2) is not necessarily established owing to the type of the other structural unit included as the case may be, but is preferably 10 to 100 mol %, and more preferably 20 to 100 mol %.

When the alkali-soluble polymer (B2) includes a structural unit having an unsaturated bond between carbon atoms such as the structural unit (5), it may be also used in the form of a hydrogenated product. The percentage of hydrogenation in this instance is typically no greater than 70%, preferably no greater than 50%, and more preferably no greater than 40% with respect to the unsaturated bond between carbon atoms included in the relevant structural unit. In this case, when the percentage of hydrogenation exceeds 70%, developability with alkali of the alkali-soluble polymer (B2) may be deteriorated.

The alkali-soluble polymer (B2) in the embodiment of the present invention is particularly preferably a polymer including poly(4-hydroxystyrene), a 4-hydroxystyrene/4-hydroxy-α-methylstyrene copolymer, a 4-hydroxystyrene/styrene copolymer or the like as a principal component.

Although Mw of the alkali-soluble polymer (B2) may vary depending on desired characteristics of the radiation-sensitive resin composition, the Mw is typically 1,000 to 150,000, and preferably 3,000 to 100,000.

In the radiation-sensitive resin composition of the embodiment of the present invention, the alkali-soluble polymer (B2) may be used either alone, or as a mixture of two or more types thereof.

Synthesis Method of Base Polymer (B)

The base polymer (B) may be prepared, for example, by polymerizing the monomer corresponding to each predetermined structural unit in an appropriate solvent using a radical polymerization initiator. For example, the base polymer (B) is preferably synthesized according to a method such as, e.g.: a method in which a solution containing a monomer and a radical initiator is added dropwise to a solution containing a reaction solvent or a monomer to permit a polymerization reaction; a method in which a solution containing a monomer, and a solution containing a radical initiator are each separately added dropwise to a solution containing a reaction solvent or a monomer to permit a polymerization reaction; and a method in which a plurality of types of solutions each containing a monomer, and a solution containing a radical initiator are each separately added dropwise to a solution containing a reaction solvent or a monomer to permit a polymerization reaction.

The reaction temperature in these methods may be appropriately predetermined depending on the type of the initiator species. The reaction temperature is typically 30° C. to 180° C., preferably 40° C. to 160° C., and more preferably 50° C. to 140° C. The time period for the dropwise addition may vary depending on the conditions such as the reaction temperature, the type of the initiator and the monomer to be reacted, and is typically 30 min to 8 hrs, preferably 45 min to 6 hrs, and more preferably 1 hour to 5 hrs. Further, the total reaction time period including time period for dropwise addition may also vary depending on the conditions similarly to the time period for the dropwise addition, and is typically 30 min to 8 hrs, preferably 45 min to 7 hrs, and more preferably 1 hour to 6 hrs.

Examples of the radical initiator for use in the polymerization include azobisisobutyronitrile (AIBN), 2,2'-azobis(4-methoxy-2,4-dimethylvaleronitrile), 2,2'-azobis(2-cyclopropylpropionitrile), 2,2'-azobis(2,4-dimethylvaleronitrile), 2,2'-azobis(2-methylpropionitrile), and the like. These initiators may be used either alone, or as a mixture of two or more thereof.

A polymerization solvent is not limited as long as the solvent is other than solvents that inhibit polymerization (nitrobenzene having a polymerization inhibitory effect, a mercapto compound having a chain transfer effect, etc.), and is capable of dissolving the monomer. Examples of the polymerization solvent include: alkanes such as n-pentane, n-hexane, n-heptane, n-octane, n-nonane and n-decane; cycloalkanes such as cyclohexane, cycloheptane, cyclooctane, decalin and norbornane; aromatic hydrocarbons such as benzene, toluene, xylene, ethylbenzene and cumene; halogenated hydrocarbons such as chlorobutanes, bromohexanes, dichloroethanes, hexamethylene dibromide and chlorobenzene; saturated carboxylate esters such as ethyl acetate, n-butyl acetate, i-butyl acetate and methyl propionate; ketones such as acetone, 2-butanone, 4-methyl-2-pentanone and 2-heptanone; ethers such as tetrahydrofuran, dimethoxyethanes and diethoxyethanes; alcohols such as methanol, ethanol, 1-propanol, 2-propanol and 4-methyl-2-pentanol; and the like. These solvents may be used either alone, or as a mixture of two or more types thereof.

The polymer obtained by the polymerization reaction may be recovered preferably by a reprecipitation technique. More specifically, after the polymerization reaction is completed, the polymerization mixture is charged into a solvent for reprecipitation, whereby a target polymer is recovered in the form of powder. As the reprecipitation solvent, an alcohol, an alkane or the like may be used either alone or as a mixture of two or more thereof. Alternatively to the reprecipitation technique, liquid separating operation, column operation, ultrafiltration operation or the like may be employed to recover the polymer through eliminating low molecular components such as monomers and oligomers.

Crosslinking Agent

In the radiation-sensitive resin composition of the embodiment of the present invention, a compound capable of crosslinking the alkali-soluble polymer (B2) in the presence of an acid (hereinafter, may be referred to as "crosslinking agent") may be blended. The crosslinking agent is exemplified by a compound having one or more functional groups having crosslinking reactivity with the alkali-soluble polymer (hereinafter, may be referred to as "crosslinkable functional group").

Examples of the crosslinkable functional group include glycidyl ether group, a glycidyl ester group, a glycidylamino group, a methoxymethyl group, an ethoxymethyl group, a benzyloxy methyl group, an acetoxy methyl group, a benzoyloxy methyl group, a formyl group, an acetyl group, a vinyl group, an isopropenyl group, a (dimethylamino)methyl group, a (diethylamino)methyl group, a (dimethylolamino) methyl group, a (diethylolamino)methyl group, a morpholinomethyl group, and the like.

Examples of the crosslinking agent include bisphenol A type epoxy compounds, bisphenol F type epoxy compounds, bisphenol S type epoxy compounds, novolak polymer type epoxy compounds, resol polymer type epoxy compounds, poly(hydroxystyrene) type epoxy compounds, methylol group-containing melamine compounds, methylol group-containing benzoguanamine compounds, methylol group-containing urea compounds, methylol group-containing phenol compounds, alkoxyalkyl group-containing melamine compounds, alkoxyalkyl group-containing benzoguanamine compounds, alkoxyalkyl group-containing urea compound, alkoxyalkyl group-containing phenol compounds, carboxymethyl group-containing melamine polymers, carboxymethyl group-containing benzoguanamine polymers, carboxymethyl group-containing urea polymers, carboxymethyl group-containing phenol polymers, carboxymethyl group-containing melamine compounds, carboxymethyl group-containing benzoguanamine compounds, carboxymethyl group-containing urea compounds, carboxymethyl group-containing phenol compounds, and the like.

Among these crosslinking agents, methylol group-containing phenol compounds, methoxymethyl group-containing melamine compounds, methoxymethyl group-containing phenol compounds, methoxymethyl group-containing glycoluril compounds, methoxymethyl group-containing urea compounds and acetoxy methyl group-containing phenol compounds are preferred, and methoxymethyl group-containing melamine compounds (for example, hexamethoxymethylmelamine, etc.), methoxymethyl group-containing glycoluril compounds, methoxymethyl group-containing urea compounds and the like are more preferred. The methoxymethyl group-containing melamine compound is commercially available under the trade names of CYMEL 300, CYMEL 301, CYMEL 303 and CYMEL 305 (all manufactured by Mitsui-Cyanamid, Ltd.), and the like; the methoxymethyl group-containing glycoluril compound is commercially available under the trade name of CYMEL 1174 (Mitsui-Cyanamid, Ltd.), and the like; and the methoxymethyl group-containing urea compound is commercially available under the trade name of MX290 (manufactured by SANWA Chemical Co., Ltd), and the like.

In addition, as the crosslinking agent, a polymer produced by substituting with a crosslinkable functional group hydrogen atoms of the oxygen-containing functional group in the alkali-soluble polymer (B2) to impart a property as a crosslinking agent may be suitably used. It is impossible to categorically define the percentage introduction of the crosslinkable functional group in this case depending on the type of the crosslinkable functional group and the alkali-soluble polymer into which the group is introduced, but the percentage introduction is typically 5 to 60 mol %, preferably 10 to 50 mol %, and more preferably 15 to 40 mol % with respect to all the oxygen-containing functional groups in the alkali-soluble polymer (B2). In this instance, the percentage introduction of the crosslinkable functional group being less than 5 mol % is likely to result in a decrease in the percentage of residual film, meandering and swelling of the pattern, and the like. To the contrary, when the percentage introduction is beyond 60 mol %, the alkali developability tends to be deteriorated.

The crosslinking agent in the embodiment of the present invention is particularly preferably a methoxymethyl group-containing compound, and more specifically, dimethoxymethylurea, tetramethoxymethyl glycoluril and the like are preferred. In the radiation-sensitive resin composition of the embodiment of the present invention, the crosslinking agent may be used either alone, or as a mixture of two or more types thereof.

The amount of the crosslinking agent used is preferably 5 to 95 parts by mass, more preferably 15 to 85 parts by mass, and particularly preferably 20 to 75 parts by mass with respect to 100 parts by mass of the alkali-soluble polymer (B2). In this instance, when the amount of the crosslinking agent used is less than 5 parts by mass, a decrease in the percentage of residual film, meandering and swelling of the pattern, and the like are likely to be caused, whereas, when the amount is beyond 95 parts by mass, the alkali developability tends to be deteriorated.

(C) Polymer

The radiation-sensitive resin composition of the embodiment of the present invention may also contain (C) a fluorine-containing polymer as a polymer additive. When a photoresist film is formed using the composition containing the base polymer (B) and the polymer (C), distribution of the polymer (C) is likely to increase on the surface of the photoresist film resulting from the water repellency of the polymer (C). In other words, the polymer (C) is unevenly distributed in the surface layer of the photoresist film. Therefore, it is not necessary to separately form an upper layer film for the purpose of blocking the photoresist film from the medium for liquid immersion lithography, and thus the radiation-sensitive resin composition can be suitably used in liquid immersion lithography process.

The polymer (C) is not particularly limited as long as it includes a fluorine atom in the molecule, and preferably includes a structural unit having a fluorine atom (hereinafter, may be referred to as "structural unit (C1)"). Specific examples of the structural unit (C1) include structural units having a fluorine atom represented by the following formulae (a1-1) to (a1-3) (hereinafter, may be also referred to as "structural units (a1-1) to (a1-3)").

When the polymer (C) includes any of the structural units (a1-1) to (a1-3), elution of an acid generating agent, an acid diffusion control agent, etc., in the resist film into a liquid for liquid immersion lithography can be suppressed. In addition, due to the polymer (C) including any of such structural units, a receding contact angle between the resist film and the liquid for liquid immersion lithography is improved, and thus water droplets originated from a liquid for liquid immersion lithography are less likely to remain on the resist film, whereby generation of defects resulting from a liquid for liquid immersion lithography can be inhibited.

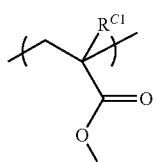

(a1-1)

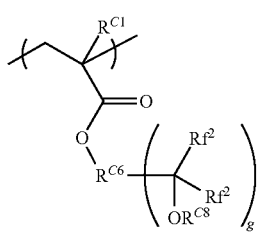

(a1-2)

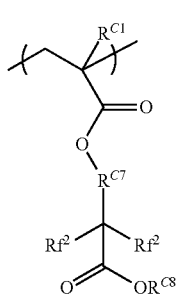

(a1-3)

In the above formulae (a1-1) to (a1-3), $R^{C1}$ represents a hydrogen atom, a methyl group or a trifluoromethyl group; $Rf^1$ represents a fluorinated alkyl group having 1 to 30 carbon atoms; $R^{C6}$ represents a linking group having a valency of (g+1); g is an integer of 1 to 3; $R^{C7}$ represents a divalent linking group; $R^{C8}$ represents a hydrogen atom, an acid-labile group or an alkali-labile group; and $Rf^2$ each independently represent a hydrogen atom, a fluorine atom or a fluorinated alkyl group having 1 to 30 carbon atoms, but any case where all $Rf^2$s represent a hydrogen atom is excluded.

Structural Unit (a1-1)

$Rf^1$ in the above formula (a1-1) is exemplified by a linear or branched alkyl group having 1 to 6 carbon atoms substituted with at least one fluorine atom, monovalent alicyclic hydrocarbon group having 4 to 20 carbon atoms substituted with at least one fluorine atom, or groups derived therefrom, and the like.

Examples of preferred monomers which give the above structural unit (a1-1) include (meth)acrylic acid trifluoromethyl ester, (meth)acrylic acid 2,2,2-trifluoroethyl ester, (meth)acrylic acid perfluoroethyl ester, (meth)acrylic acid perfluoro-n-propyl ester, (meth)acrylic acid perfluoro-1-propyl ester, (meth)acrylic acid perfluoro-n-butyl ester, (meth)acrylic acid perfluoro-1-butyl ester, (meth)acrylic acid perfluoro-t-butyl ester, (meth)acrylic acid 2-(1,1,1,3,3,3-hexafluoropropyl) ester, (meth)acrylic acid 1-(2,2,3,3,4,4,5,5-octafluoropentyl) ester, (meth)acrylic acid perfluorocyclohexylmethyl ester, (meth)acrylic acid 1-(2,2,3,3,3-pentafluoropropyl) ester, (meth)acrylic acid 1-(3,3,4,4,5,5,6,6,7,7,8,8,9,9,10,10,10-heptadecafluorodecyl) ester, (meth)acrylic acid 1-(5-trifluoromethyl-3,3,4,4,5,6,6,6-octafluorohexyl) ester, and the like.

Structural Units (a1-2) and (a1-3)

In the above formulae (a1-2) and (a1-3), $R^{C8}$ represents a hydrogen atom or a monovalent organic group. Examples of the monovalent organic group include monovalent hydrocarbon groups having 1 to 30 carbon atoms, acid-labile groups, alkali-labile groups, and the like.

The monovalent hydrocarbon group having 1 to 30 carbon atoms is exemplified by linear or branched monovalent hydrocarbon groups having 1 to 10 carbon atoms, monovalent cyclic hydrocarbon group having 3 to 30 carbon atoms, and the like. With respect to these hydrocarbon groups, the definition of the hydrocarbon group in connection with $R^1$ in the above formula (1) may be directly applied, but those involved in acid-labile groups and alkali-labile groups described later are excluded. Moreover, the hydrocarbon group may have a substituent. With respect to the substituent, the definition of the substituent which may be included in $R^1$ described above may be directly applied.

Specific examples of the acid-labile group include a t-butoxycarbonyl group, a tetrahydropyranyl group, a tetrahydrofuranyl group, a (thiotetrahydropyranylsulfanyl)methyl group, a (thiotetrahydrofuranylsulfanyl)methyl group, as well as an alkoxy-substituted methyl group, an alkylsulfanyl-substituted methyl group, and the like. It is to be noted that the alkoxyl group that is a substituent in the alkoxy-substituted methyl group is exemplified by an alkoxyl group having 1 to 4 carbon atoms. In addition, the alkyl group that is a substituent in the alkylsulfanyl-substituted methyl group is exemplified by an alkyl group having 1 to 4 carbon atoms.

The acid-labile group is exemplified by a group represented by a formula of: —C(R)$_3$. Wherein, in the formula, with respect to three $R^5$, the definition of $R^7$ to $R^9$ in the above formula (2) may be applied.

Among these, the group represented by the above formula —C(R)$_3$, a t-butoxycarbonyl group, and an alkoxy-substituted methyl group are preferred. In particular, in the structural unit (a1-2), a t-butoxycarbonyl group and an alkoxy-substituted methyl group are preferred. In the structural unit (a1-3), an alkoxy-substituted methyl group and the group represented by the formula of: —C(R)$_3$ are preferred.

Use of the acid-labile group described above as the structural unit (a1-2) and structural unit (a1-3) is preferred, since improvement of the solubility of the polymer (C) at the site exposed with a radioactive ray is enabled when used in combination with the base polymer (B) described above. This benefit is believed to result from generation of a polar group through a reaction of the acid-labile group with an acid generated at a light-exposed site of the resist film in the exposure step of a resist pattern-forming method described later.

The "alkali-labile group" as referred to means a group that substitutes for a hydrogen atom in a polar functional group such as for example, a hydroxyl group or a carboxyl group and is dissociated in the presence of an alkali.

Such an alkali-labile group is not particularly limited as long as the aforementioned properties are exhibited, and the alkali-labile group in the above formula (a1-2) is exemplified by groups represented by the following formula (R1-1).

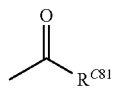

(R1-1)

In the above formula (R1-1), $R^{C81}$ represents a hydrocarbon group having 1 to 10 carbon atoms in which at least one hydrogen atom(s) is/are substituted by a fluorine atom. With respect to $R^{C81}$, the definition of $Rf^1$ described above may be applied.

$R^{C81}$ is preferably a linear or branched perfluoroalkyl group having 1 to 10 carbon atoms in which all hydrogen atoms in the hydrocarbon group are substituted by a fluorine atom, and more preferably a trifluoromethyl group.

The alkali-labile group in the above formula (a1-3) is exemplified by groups represented by the following formulae (R1-2) to (R1-4).

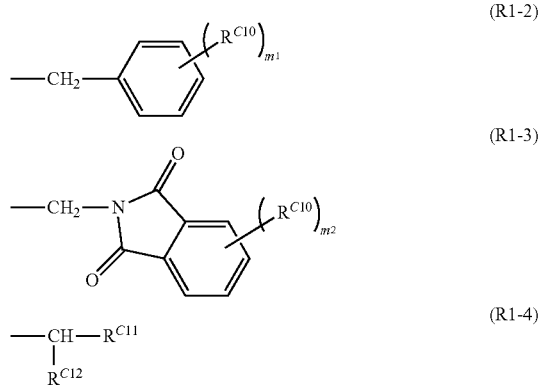

In the above formulae (R1-2) and (R1-3), $R^{C10}$ represents a halogen atom, an alkyl group, an alkoxyl group, an acyl group, or an acyloxy group having 1 to 10 carbon atoms; $m_1$ is an integer of 0 to 5; and $m_2$ is an integer of 0 to 4, wherein in the case where $m_1$ and $m_2$ are each 2 or greater, $R^{C10}$s present in a plurality of are each identical or different. In the above formula (R1-4), $R^{C11}$ and $R^{C12}$ each independently represent a hydrogen atom or an alkyl group having 1 to 10 carbon atoms, and optionally $R^{C11}$ and $R^{C12}$ bond to one another to taken together represent an alicyclic structure having 4 to 20 carbon atoms.

In the above formulae (R1-2) and (R1-3), examples of the halogen atom represented by $R^{C10}$ include a fluorine atom, a chlorine atom, a bromine atom, an iodine atom, and the like. Of these, a fluorine atom is preferred.

In the above formula (R1-2) and (R1-3), $R^{C10}$ preferably represents an alkyl group having 1 to 10 carbon atoms.

Examples of the alicyclic structure taken together represented by $R^{C11}$ and $R^{C12}$ bonded to one another together with the carbon atom to which $R^{C11}$ and $R^{C12}$ each bond include a cyclopentyl group, a cyclopentylmethyl group, a 1-(1-cyclopentylethyl) group, a 1-(2-cyclopentylethyl) group, a cyclohexyl group, a cyclohexylmethyl group, a 1-(1-cyclohexylethyl) group, a 1-(2-cyclohexylethyl) group, a cycloheptyl group, a cycloheptylmethyl group, a 1-(1-cycloheptylethyl) group, a 1-(2-cycloheptylethyl) group, a 2-norbornyl group, and the like.

Specific examples of the group represented by the above formula (R1-4) include a methyl group, an ethyl group, a 1-propyl group, a 2-propyl group, a 1-butyl group, a 2-butyl group, a 1-pentyl group, a 2-pentyl group, a 3-pentyl group, a 1-(2-methylbutyl) group, a 1-(3-methylbutyl) group, a 2-(3-methylbutyl) group, a neopentyl group, a 1-hexyl group, a 2-hexyl group, a 3-hexyl group, a 1-(2-methylpentyl) group, a 1-(3-methylpentyl) group, a 1-(4-methylpentyl) group, a 2-(3-methylpentyl) group, a 2-(4-methylpentyl) group, a 3-(2-methylpentyl) group, and the like. Of these, a methyl group, an ethyl group, a 1-propyl group, a 2-propyl group, a 1-butyl group and a 2-butyl group are preferred.

Including the alkali-labile group as described above in the structural unit (a1-2) or the structural unit (a1-3) in the polymer (C) is preferred since an affinity of the polymer (C) to a developer solution can be improved. This benefit is believed to result from generation of a polar group through a reaction of the alkali-labile group included in the polymer (C) with a developer solution in the development step of a method for forming a pattern described later.

In the above formulae (a1-2) and (a1-3), in the case in which $R^{C8}$ represents a hydrogen atom, the structural units (a1-2) and (a1-3) will have a hydroxyl group and a carboxy group which are each a polar group. When the polymer (C) has such a structural unit, an affinity of the polymer (C) to the developer solution can be improved in the development step of a method for forming a pattern described later.

In the above formula (a1-2), $R^{C6}$ represents a linking group having a valency of (g+1). The linking group is exemplified by a single bond, a hydrocarbon group having 1 to 30 carbon atoms and having a valency of (g+1), and the like. Alternatively, groups derived by combining any of these hydrocarbon groups with a sulfur atom, an imino group, a carbonyl group, —CO—O— or —CO—NH—. "g" is an integer of 1 to 3. When g is 2 or 3, a plurality of $R^{C8}$s are each identical or different and $Rf^2$s in the formula (a1-2) are each identical or different, and groups which may be represented by the following formula are each independent.

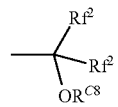

Among the hydrocarbon group having a valency of (g+1) represented by $R^{C6}$, examples of chain hydrocarbon group include groups derived by removing (g+1) hydrogen atoms from a chain hydrocarbon having 1 to 10 carbon atoms such as methane, ethane, propane, butane, 2-methylpropane, pentane, 2-methylbutane, 2,2-dimethylpropane, hexane, heptane, octane, nonane or decane, and the like.

Among the hydrocarbon group having a valency of (g+1) represented by $R^{C6}$, examples of $R^{C6}$ having a cyclic structure include groups derived by removing (g+1) hydrogen atoms from an alicyclic hydrocarbon having 4 to 20 carbon atoms such as cyclobutane, cyclopentane, cyclohexane, bicyclo[2.2.1]heptane, bicyclo[2.2.2]octane, tricyclo[5.2.1.02,6]decane or tricyclo[3.3.1.13,7]decane, and groups derived by removing (g+1) hydrogen atoms from an aromatic hydrocarbon having 6 to 30 carbon atoms such as benzene or naphthalene, and the like.

Among $R^{C6}$s, examples of the structure having an oxygen atom, a sulfur atom, an imino group, a carbonyl group, —CO—O— or —CO—NH— include those represented by the following formulae.

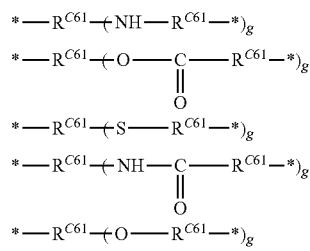

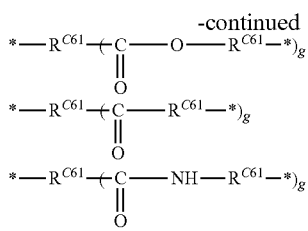

In the above formula, $R^{C61}$ each independently represents a single bond, a divalent chain hydrocarbon group having 1 to 10 carbon atoms, a divalent cyclic hydrocarbon group having 4 to 20 carbon atoms or a divalent aromatic hydrocarbon group having 6 to 30 carbon atoms.

Also, $R^{C6}$ may have a substituent.

With respect to the linking group represented by $R^{C7}$ in the above formula (a1-3), the definition of the linking group represented by $R^{C6}$ described above may be applied. Wherein, g is 1.

In the above formulae (a1-2) and (a1-3), $Rf^2$ represents a hydrogen atom, a fluorine atom or a fluorinated hydrocarbon group having 1 to 30 carbon atoms, wherein, any case where all $Rf^2$s represent a hydrogen atom is excluded. With respect to the fluorinated hydrocarbon group having 1 to 30 carbon atoms represented by $Rf^2$, the definition of $Rf^1$ may be directly applied.

In the above formulae (a1-2) and (a1-3), a partial structure represented by the following formula including $Rf^2$ is exemplified by structures represented by the following formulae (1) to (5), and the like.

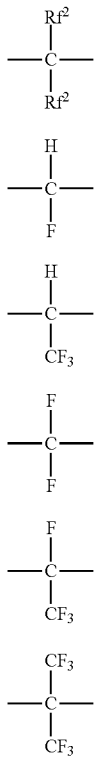

Of these, in the above formula (a1-2), a structure represented by the following formula (5) is preferred, whereas in the above formula (a1-3), a structure represented by the following formula (3) is preferred.

Specific examples of the structural unit (a1-2) include structural units represented by the following formulae (a1-2-1) and (a1-2-2), and the like.

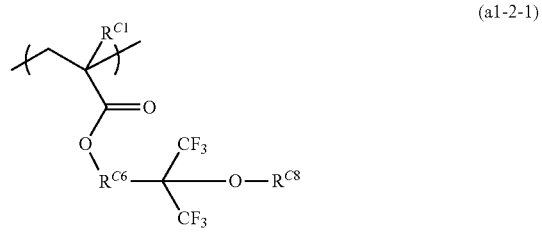

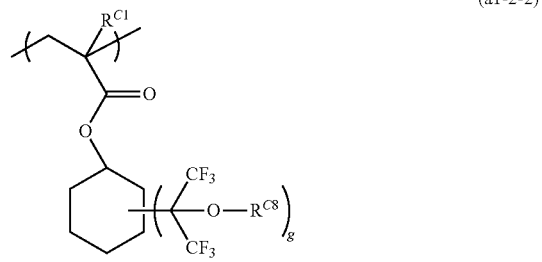

In the above formulae (a1-2-1) and (a1-2-2), $R^{C1}$, $R^{C6}$, $R^{C8}$ and g are as defined in the above formula (a2-1).

Examples of compounds that give such a structural unit include compounds represented by the following formulae.

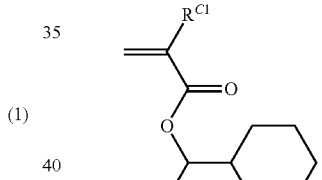
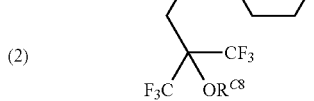
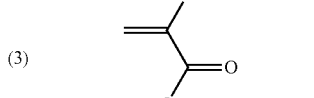
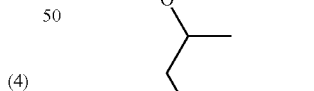
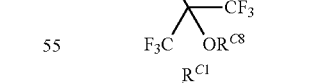
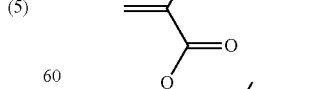
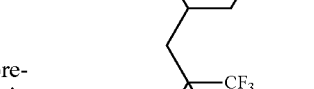

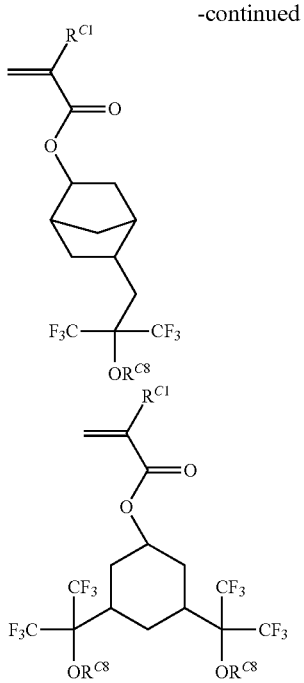

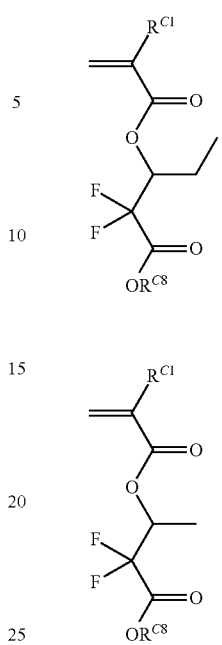

In the above formulae, $R^{C1}$, and $R^{C8}$ are as defined in the above formula (a1-2).

The compound represented by the above formula, in which $R^{C8}$ represents an acid-labile group or an alkali-labile group can be synthesized using as a raw material, for example, a compound represented by each formula in which $R^{C8}$ represents a hydrogen atom. Referring to an exemplary compound in which $R^{C8}$ is represented by the above formula (R1-1), the intended compound represented by the above formula can be synthesized by fluoroacylating a compound represented by each formula in which $R^{C8}$ represents a hydrogen atom according to a conventionally well-known method. For example, 1) a method including allowing an alcohol and a fluorocarboxylic acid to be condensed in the presence of an acid, thereby permitting esterification, 2) a method including allowing an alcohol and a fluorocarboxylic acid halide to be condensed in the presence of a base, thereby permitting esterification, and the like may be exemplified.

Specific examples of the structural unit (a1-3) include structural units represented by the following formula.

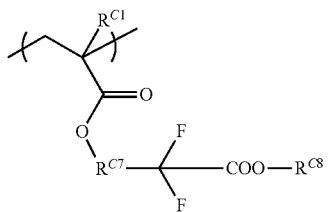

In the above formula (a1-3-1), $R^{C1}$, $R^{C7}$ and $R^{C8}$ are as defined in the above formula (a1-3).

Examples of compounds that give such a structural unit include compounds represented by the following formulae.

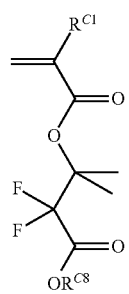

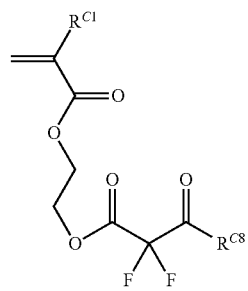

In the above formula (a1-3-1), $R^{C1}$ and $R^{C8}$ are as defined in the above formula (a1-3).

The compound represented by the above formula, in which $R^{C8}$ represents an acid-labile group or an alkali-labile group can be synthesized using as a raw material, for example, a compound represented by each formula in which $R^{C8}$ represents a hydrogen atom, or a derivative thereof. Referring to an exemplary compound in which $R^{C8}$ is represented by the above formula (R1-4), this compound can be obtained by allowing, for example, a compound represented by the following formula (m-2-3) to react with a compound represented by the following formula (m-2-4-3).

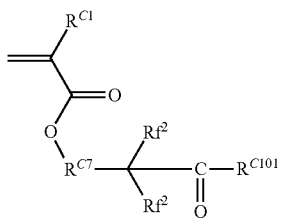

(m-2-3)

In the above formula (m-2-3), $R^{C1}$, $R^{C7}$ and $Rf^2$ are as defined in the above formula (a1-3); and $R^{C101}$ represents a hydroxyl group or a halogen atom.

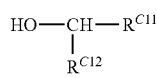

(m-2-4-3)

In the above formula (m-2-4-3), $R^{C11}$ and $R^{C12}$ are as defined in the above formula (R1-4).

The polymer (C) may include only one type of the above structural units (a1-1) to (a1-3), or two or more thereof, and preferably has at least two types of the structural units (a1-1) to (a1-3). Any combination of the structural unit (a1-2) and the structural unit (a1-3) is particularly preferred.

The polymer (C) may further include in addition to the structural units (a1-1) to (a1-3): a structural unit having other acid-labile group (hereinafter, may be also referred to as "structural unit (C2)"), a structural unit (C3) having other alkali-soluble group (hereinafter, may be referred to as "structural unit (C3)"), or a structural unit (C4) having a lactone skeleton (hereinafter, may be referred to as "structural unit (C4)").

Structural Unit (C2)

When a polymer having the structural unit (C2) is used as the polymer (C), use in combination with the acid-labile group-containing polymer (B1) is particularly preferred for a positive type radiation-sensitive resin composition. In this case, the difference between an advancing contact angle and a receding contact angle of the photoresist film can be decreased, thereby capable of meeting a scanning speed in exposure.

The structural unit (C2) is preferably represented by the following formula (C2-1-1).

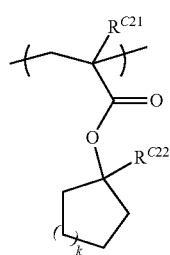

(C2-1-1)

In the above formula (C2-1-1), $R^{C21}$ represents a hydrogen atom, a methyl group, a trifluoromethyl group or a hydroxymethyl group; $R^{C22}$ represents a linear or branched alkyl group having 1 to 4 carbon atoms; and k is an integer of 1 to 4.

In the above formula (C2-1-1), examples of the linear or branched alkyl group having 1 to 4 carbon atoms represented by $R^{C22}$ include a methyl group, an ethyl group, a n-propyl group, an i-propyl group, a n-butyl group, a 2-methylpropyl group, a 1-methylpropyl group, a t-butyl group, and the like.

The polymer (C) may include the structural unit (C2) either one type alone or in combination of two or more types thereof. The polymer (C) which may be used further include the structural unit (C3) or the structural unit (C4) in addition to the structural units (C1) and (C2). In this case, solubility in a developer solution can be improved.

Structural Unit (C3)

The alkali-soluble group in the structural unit (C3) is preferably a functional group having a hydrogen atom and having a pKa of 4 to 11, in light of improvement of the solubility in a developer solution. Specific examples of such a functional group include functional groups represented by the following formula (C3a) and formula (C3b), and the like.

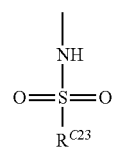

(C3a)

(C3b)

In the above formula (C3a), $R^{C23}$ represents a hydrocarbon group having 1 to 10 carbon atoms substituted with a fluorine atom.

In the above formula (C3a), the hydrocarbon group having 1 to 10 carbon atoms substituted with a fluorine atom represented by $R^{C23}$ is not particularly limited as long as one, or two or more hydrogen atoms in the hydrocarbon group having 1 to 10 carbon atoms is/are substituted by a fluorine atom, and a trifluoromethyl group and the like are preferred.

The main chain skeleton of the structural unit (C3) is not particularly limited, and is preferably a skeleton of a methacrylic acid ester, an acrylic acid ester, or an α-trifluoro acrylic acid ester.

Examples of the structural unit (C3) include structural units derived from compounds represented by the following formulae (C3a-1) and (C3b-1), and the like.

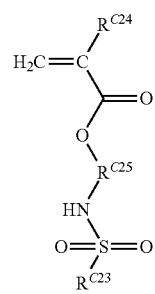

(C3a-1)

-continued

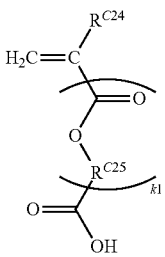

(C3b-1)

In the above formula, $R^{C24}$ represents a hydrogen atom, a methyl group, or a trifluoromethyl group; $R^{C25}$ represents a divalent linking group; $R^{C23}$ is as defined in the above formula (C3a); and k1 is 0 or 1.

In the above formula (C3a-1) and (C3b-1), with respect to the group represented by $R^{C25}$, the definition of $R^{C7}$ in the above formula (a1-3) may be applied.

The (C) polymer may include the structural unit (C3) either alone or in combination of two or more types thereof.

Structural Unit (C4)

Specifically, the structural unit (C4) is exemplified by a structural unit having a lactone skeleton (hereinafter, may be referred to as "structural unit (C4-1)"). With respect to the structural unit (C4-1), the definition of the structural unit (2) in connection with the acid-labile group-containing polymer (B1) may be applied.

The proportion of each structural unit contained with respect to 100 mol % in total of the entire structural units in the polymer (C) is shown below. The proportion of the structural unit (C1) contained is preferably 20 to 90 mol %, and more preferably 20 to 80 mol %. In addition, the proportion of the structural unit (C2) contained is typically no greater than 80 mol %, preferably 20 to 80 mol %, and more preferably 30 to 70 mol %. The proportion of the structural unit (C2) contained falling within this range is particularly preferred in light of a decrease in the difference between the advancing contact angle and the receding contact angle. The proportion of the structural unit (C3) contained is typically no greater than 50 mol %, preferably 5 to 30 mol %, and more preferably 5 to 20 mol %. The proportion of the structural unit (C4) contained is typically no greater than 50 mol %, preferably 5 to 30 mol %, and more preferably 5 to 20 mol %.

The polymer (C) may be prepared, for example, by polymerizing a polymerizable unsaturated monomer corresponding to each predetermined structural unit in an appropriate solvent using a radical polymerization initiator such as a hydroperoxide, dialkylperoxide, diacylperoxide, azo compound or the like, in the presence of a chain transfer agent if necessary.

The weight average molecular weight of the polymer (C) in terms of a polystyrene equivalent as determined by a gel permeation chromatography (GPC) method (hereinafter, may be referred to as "Mw") is preferably 1,000 to 50,000, more preferably 1,000 to 40,000, and still more preferably 1,000 to 30,000. When the Mw is less than 1,000, obtaining a photoresist film having a sufficient receding contact angle may fail. On the other hand, when the Mw exceeds 50,000, the developability of the photoresist film may be deteriorated. In addition, a ratio (Mw/Mn) of the Mw to the number average molecular weight in terms of a polystyrene equivalent as determined by a GPC method (hereinafter, may be referred to as "Mn") of the polymer (C) is preferably 1 to 5, and more preferably 1 to 4.

The polymer (C) preferably has a content of impurities such as halogen and metals being as low as possible. When the content of such impurities is low, the sensitivity, resolution, process stability, pattern configuration and the like of the photoresist film can be further improved.

The content of the polymer (C) is preferably 0.1 to 20 parts by mass, more preferably 1 to 10 parts by mass, and still more preferably 1 to 7.5 parts by mass with respect to 100 parts by mass of the base polymer (B). When the content of the polymer (C) is less than 0.1 parts by mass, the effects achieved by including the polymer (C) may not be sufficiently achieved. On the other hand, when the content is greater than parts by mass, water repellency of the surface of the resist film may be so great that development defects may occur.

The proportion of the fluorine atoms contained in the polymer (C) is typically no less than 5% by mass, preferably 5 to 50% by mass, and more preferably 5 to 40% by mass with respect to 100% by mass of the entirety of the polymer (C). It is to be noted that the proportion of fluorine atoms contained may be determined by $^{13}$C-NMR. When the proportion of fluorine atoms contained in the polymer (C) falls within the above range, water repellency of the surface of the photoresist film formed from the radiation-sensitive resin composition containing the polymer (C) and the polymer (B) described above can be improved, and thus it is not necessary to separately form an upper layer film in liquid immersion lithography.

Synthesis Method of Polymer (C)

The polymer (C) may be prepared, for example, by polymerizing a polymerizable unsaturated monomer corresponding to each predetermined structural unit in an appropriate solvent using a radical polymerization initiator such as a hydroperoxide, dialkylperoxide, diacylperoxide, azo compound or the like, in the presence of a chain transfer agent if necessary. It is to be noted that with respect to the synthesis method, details of the synthesis method of the base polymer (B) may be applied.

Acid Diffusion Control Agent

Into the radiation-sensitive resin composition of the embodiment of the present invention is preferably blended an acid diffusion control agent that controls a phenomenon of diffusion in the resist coating film of an acid generated from the radiation-sensitive acid generating agent by exposure, thereby inhibiting an undesired chemical reaction in an unexposed area. By blending such an acid diffusion control agent, storage stability of the radiation-sensitive resin composition can have improved. In addition, the resolution is further improved, and an alteration of a line width of the resist pattern due to varying post-exposure delay (PED) from the exposure to the development process to be prevented. As a result, a radiation-sensitive resin composition that is extremely superior in process stability can be obtained.

Such an acid diffusion control agent is exemplified by nitrogen-containing organic compounds disclosed in WO 2009/051088, in paragraphs [0176] to [0187], and the like. The nitrogen-containing organic compound is exemplified by: amino compounds having one nitrogen atom in an identical molecule; diamino compounds having two nitrogen atom in an identical molecule; polyamino compounds having three or more nitrogen atoms in an identical molecule; amide group-containing compounds, urea compounds, nitrogen-containing heterocyclic compounds, nitrogen-containing organic compounds having an acid-labile group, and the like.

Examples of the amino compound include: monoalkylamines such as n-hexylamine, n-heptylamine, n-octylamine, n-nonylamine and n-decylamine; dialkylamines such as di-n-butylamine, di-n-pentylamine, di-n-hexylamine, di-n-heptylamine, di-n-octylamine, di-n-nonylamine and di-n-decylamine; trialkylamines such as triethylamine, tri-n-propylamine, tri-n-butylamine, tri-n-pentylamine, tri-n-hexylamine, tri-n-heptylamine, tri-n-octylamine, tri-n-nonylamine and tri-n-decylamine; alkanolamines such as ethanolamine, diethanolamine and triethanolamine; aromatic amines such as aniline, N-methylaniline, N,N-dimethyl aniline, 2-methylaniline, 3-methylaniline, 4-methylaniline, 4-nitroaniline, diphenylamine, triphenylamine and 1-naphthylamine, and the like.

Examples of the diamino compound include ethylenediamine, N,N,N',N'-tetramethylethylenediamine, tetramethylenediamine, hexamethylenediamine, N,N,N',N'-tetrakis(2-hydroxyethyl)ethylenediamine, N,N,N',N'-tetrakis(2-hydroxypropyl)ethylenediamine, 4,4'-diaminodiphenylmethane, 4,4'-diaminodiphenyl ether, 4,4'-diaminobenzophenone, 4,4'-diaminodiphenylamine, 2,2'-bis(4-aminophenyl)propane, 2-(3-aminophenyl)-2-(4-aminophenyl)propane, 2-(4-aminophenyl)-2-(3-hydroxyphenyl)propane, 2-(4-aminophenyl)-2-(4-hydroxyphenyl)propane, 1,4-bis[1-(4-aminophenyl)-1-methylethyl]benzene, 1,3-bis[1-(4-aminophenyl)-1-methylethyl]benzene, and the like. Examples of the polyamino compound include polyethyleneimine, polyallylamine, polymers of N-(2-dimethylaminoethyl)acrylamide, and the like.

Examples of the amide group-containing compound include formamide, N-methylformamide, N,N-dimethylformamide, acetamide, N-methylacetamide, N,N-dimethylacetamide, propionamide, benzamide, pyrrolidone, N-methylpyrrolidone, and the like.

Examples of the urea compound include urea, methylurea, 1,1-dimethylurea, 1,3-dimethylurea, 1,1,3,3-tetramethylurea, 1,3-diphenylurea, tri-n-butylthiourea, and the like.

Examples of the nitrogen-containing heterocyclic compound include: imidazoles such as imidazole, benzimidazole, 2-methylimidazole, 4-methylimidazole, 1,2-dimethyl imidazole, 2-phenylimidazole, 4-phenylimidazole, 4-methyl-2-phenylimidazole and 2-phenylbenzimidazole; pyridines such as pyridine, 2-methylpyridine, 4-methylpyridine, 2-ethylpyridine, 4-ethylpyridine, 2-phenylpyridine, 4-phenylpyridine, 2-methyl-4-phenylpyridine, nicotine, nicotinic acid, nicotinic amide, quinoline, 8-oxyquinoline and acridine, as well as pyrazine, pyrazole, pyridazine, quinoxaline, purine, pyrrolidine, piperidine, 1-piperidine ethanol, 2-piperidine ethanol, morpholine, 4-methylmorpholine, piperazine, 1,4-dimethylpiperazine, 1,4-diazabicyclo[2.2.2]octane, and the like.

Examples of the nitrogen-containing organic compound having an acid-labile group include N-(t-butoxycarbonyl)piperidine, N-(t-butoxycarbonyl)imidazole, N-(t-butoxycarbonyl)benzimidazole, N-(t-butoxycarbonyl)-2-phenylbenzimidazole, N-(t-butoxycarbonyl)di-n-octylamine, N-(t-butoxycarbonyl)diethanolamine, N-(t-butoxycarbonyl) dicyclohexylamine, N-(t-butoxycarbonyl)diphenylamine, tert-butyl-4-hydroxy-1-piperidine carboxylate, and the like.

Of these nitrogen-containing organic compounds, the amino compounds, the diamino compounds, the nitrogen-containing heterocyclic compounds, and nitrogen-containing organic compound having an acid-labile group are preferred.

Alternatively, a compound represented by the following formula (D1-0) may be also used as the acid diffusion control agent.

$$X^+Z^- \quad (D1\text{-}0)$$

In the above formula (D1-0), $X^+$ is a cation represented by the following formula (D1-1) or (D1-2); and $Z^-$ is $OH^-$ or an anion represented by $R^{D1}$—$COO^-$; and $R^{D1}$ represents an unsubstituted or substituted alkyl group, alicyclic hydrocarbon group or aryl group.

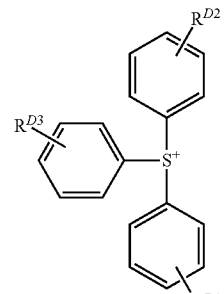

(D1-1)

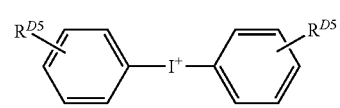

(D1-2)

In the above formula (D1-1), $R^{D2}$ to $R^{D4}$ each independently represent a hydrogen atom, an alkyl group, an alkoxyl group, a hydroxyl group, or a halogen atom.

In the above formula (D1-2), $R^{D5}$ and $R^{D6}$ each independently represent a hydrogen atom, an alkyl group, an alkoxyl group, a hydroxyl group, or a halogen atom.

The compound is used as an acid diffusion control agent that is degraded by exposure and lose acid diffusion controllability (hereinafter, may be also referred to as "photodegradable acid diffusion control agent"). Due to including the compound, an acid is diffused at sites exposed with light whereas diffusion of an acid is controlled at sites not exposed with light, thereby enabling a superior contrast between the site exposed with light and the site not exposed with light to be attained. Therefore, in particular, LWR and MEEF of the radiation-sensitive resin composition of the embodiment of the present invention can be effectively improved.

$R^{D2}$ to $R^{D4}$ preferably represent a hydrogen atom, an alkyl group, an alkoxy group or a halogen atom due to having an effect of decreasing the solubility of the compound in the developer solution. In addition, $R^{D5}$ and $R^{D6}$ preferably represent a hydrogen atom, an alkyl group or a halogen atom.

Examples of the unsubstituted or substituted alkyl group represented by $R^{D1}$ include groups having one or more substituent such as e.g.: hydroxyalkyl groups having 1 to 4 carbon atoms such as a hydroxymethyl group, a 1-hydroxyethyl group, a 2-hydroxyethyl group, a 1-hydroxypropyl group, a 2-hydroxypropyl group, a 3-hydroxypropyl group, a 1-hydroxybutyl group, a 2-hydroxybutyl group, a 3-hydroxybutyl group and a 4-hydroxybutyl group; alkoxyl groups having 1 to 4 carbon atoms such as a methoxy group, an ethoxy group, a n-propoxy group, an i-propoxy group, a n-butoxy group, a 2-methylpropoxy group, a 1-methylpropoxy group and a t-butoxy group; a cyano group; cyanoalkyl groups having 2 to 5 carbon atoms such as a cyanomethyl group, a 2-cyanoethyl group, a 3-cyanopropyl group and a 4-cyanobutyl group, and the like. Of these, a hydroxymethyl group, a cyano group and a cyanomethyl group are preferred.

Examples of the unsubstituted or substituted alicyclic hydrocarbon group represented by $R^{D1}$ include cycloalkane skeletons such as hydroxycyclopentane, hydroxycyclohexane and cyclohexanone; monovalent groups derived from an alicyclic hydrocarbon of a bridged alicyclic skeleton such as 1,7,7-trimethylbicyclo[2.2.1]heptan-2-one (camphor), and the like. Of these, groups derived from 1,7,7-trimethyl bicyclo[2.2.1]heptan-2-one are preferred.

Examples of the unsubstituted or substituted aryl group represented by $R^{D1}$ include a phenyl group, a benzyl group, a phenylethyl group, a phenylpropyl group, a phenylcyclohexyl group, and the like, as well as groups derived by substituting these compounds with a hydroxyl group, a cyano group, etc., and the like. Of these, a phenyl group, a benzyl group and a phenylcyclohexyl group are preferred.

$R^{D1}$ preferably represents an alicyclic hydrocarbon group or an aryl group due to having an effect of lowering the solubility of the compound in a developer solution.

It is to be noted that $Z^-$ in the above formula (D1-0) is preferably an anion represented by the following formula (Ia) or an anion represented by the following formula (Ib).

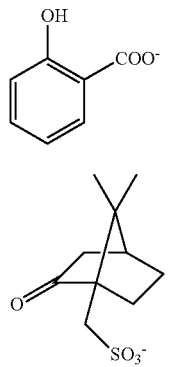

The photodegradable acid diffusion control agent is one represented by the above formula (D1-0), and specifically, a sulfonium salt compound or an iodonium salt compound that satisfies the aforementioned requirements.

Examples of the sulfonium salt compound include triphenylsulfonium hydroxide, triphenylsulfonium acetate, triphenylsulfonium salicylate, diphenyl-4-hydroxyphenylsulfonium hydroxide, diphenyl-4-hydroxyphenylsulfonium acetate, diphenyl-4-hydroxyphenylsulfonium salicylate, triphenylsulfonium 10-camphorsulfonate, 4-t-butoxyphenyldiphenylsulfonium 10-camphorsulfonate, and the like. It is to be noted that these sulfonium salt compounds may be used either alone or in combination of two or more thereof.

Moreover, examples of the iodonium salt compound include bis(4-t-butylphenyl)iodonium hydroxide, bis(4-t-butylphenyl)iodonium acetate, bis(4-t-butylphenyl)iodonium hydroxide, bis(4-t-butylphenyl)iodonium acetate, bis(4-t-butylphenyl)iodonium salicylate, 4-t-butylphenyl-4-hydroxyphenyliodonium hydroxide, 4-t-butylphenyl-4-hydroxyphenyliodonium acetate, 4-t-butylphenyl-4-hydroxyphenyliodonium salicylate, bis(4-t-butylphenyl)iodonium 10-camphorsulfonate, diphenyliodonium 10-camphorsulfonate, and the like. It is to be noted that iodonium salt compounds may be used either alone or in combination of two or more thereof.

The acid diffusion control agent may be used either alone, or as a mixture of two or more types thereof.

The amount of the acid diffusion control agent blended is preferably no greater than 15 parts by mass, more preferably 0.001 to 10 parts by mass, and still more preferably 0.005 to 5 parts by mass with respect to 100 parts by mass of the base polymer (B). In this case, when the amount of the acid diffusion control agent blended is no less than 0.001 parts by mass, deterioration of the pattern configuration and/or dimension fidelity depending on the process conditions can be inhibited, whereas when the amount is no greater than 15 parts by mass, the sensitivity and/or alkali developability as a resist can be further improved.

The radiation-sensitive resin composition may contain a dissolution control agent, a surfactant, a sensitizing agent, a lactone compound and the like as other optional components, within a range not leading to impairment of the effects of the embodiment of the present invention.

Dissolution Control Agent

Into the radiation-sensitive resin composition of the embodiment of the present invention may be blended a dissolution control agent having a property that solubility in an alkaline developer solution is enhanced by an action of an acid.

Surfactant

Into the radiation-sensitive resin composition of the embodiment of the present invention may be also blended a surfactant having an effect of improving coating properties, striation, developability and the like of the radiation-sensitive resin composition.

Sensitizing Agent

Into the radiation-sensitive resin composition of the embodiment of the present invention may be also blended a sensitizing agent capable of absorbing energy of a radioactive ray, and transmitting the energy to a radiation-sensitive acid generator, thereby increasing the amount of the acid produced to improve apparent sensitivity of the radiation-sensitive resin composition.

Lactone Compound

The lactone compound has an effect of efficiently segregating the polymer (C) on the surface of the resist film, the polymer (C) having an action of allowing water repellency to be expressed on the surface of the resist film in liquid immersion lithography. Thus, due to including the lactone compound when the polymer (C) is used, the amount of the polymer (C) added can be reduced. As a result, elution of a component from a resist film to a liquid for liquid immersion can be inhibited without impairing basic characteristics as a resist. In addition, defects derived from liquid immersion lithography such as watermark defects can be inhibited since no droplets remain even if liquid immersion lithography is carried out by high-speed scanning.

Examples of the lactone compound include gamma-butyrolactone, valerolactone, mevalonic lactone, norbornanelactone, and the like.

The radiation-sensitive resin composition according to the embodiment of the present invention may contain the lactone compound of only one type, or two or more types thereof.

The content of the lactone compound in the radiation-sensitive resin composition of the embodiment of the present invention is typically 30 to 200 parts by mass, and preferably 50 to 150 parts by mass with respect to 100 parts by mass of the base polymer (B). When the content of the lactone compound (E) is too small, water repellency of the surface of the resist film cannot be sufficiently attained in adding a small amount of the polymer (C). On the other hand, when the content is excessive, basic performances of the resist and pattern configuration after the development may be significantly deteriorated.

Furthermore, into the radiation-sensitive resin composition of the embodiment of the present invention may be blended additives other than those described in the foregoing such as, for example, a dye, a pigment, an adhesion promoter, a halation inhibitor, a storage stabilizer, a defoaming agent and a shape improving agent, specifically 4-hydroxy-4'-methylchalcone, or the like as needed within the range not leading to impairment of the effects of the present invention. In this case, due to blending a dye or a pigment, a latent image of the light-exposed site can be visualized to mitigate the influences from halation in the exposure. Moreover, due to blending an adhesion promoter, adhesiveness to the substrate can be improved.

Preparation of Radiation-Sensitive Resin Composition

The radiation-sensitive resin composition of the embodiment of the present invention is prepared, in general, by dissolving each component in a solvent in use to give a homogenous solution, and thereafter filtering through, for example, a filter having a pore size of about 0.2 µm or the like as needed.

The solvent is exemplified by ethers, esters, ether esters, ketones, ketone esters, amides, amide esters, lactams, (halogenated) hydrocarbons, and the like. More specifically, examples of the solvent include ethylene glycol monoalkyl ethers, diethylene glycol dialkyl ethers, propylene glycol monoalkyl ethers, propylene glycol dialkyl ethers, ethylene glycol monoalkyl ether acetates, propylene glycol monoalkyl ether acetates, acyclic or cyclic ketones, ester acetates, hydroxy ester acetates, alkoxy ester acetates, aceto ester acetates, propionic acid esters, lactic acid esters, pyruvic acid esters, N,N-dialkylformamides, N,N-dialkylacetamides, N-alkylpyrrolidones, (halogenated) aliphatic hydrocarbons, (halogenated) aromatic hydrocarbons, and the like.

Specific examples of the solvent include those described in e.g., WO 2009/051088, paragraph no. [0202].

Among these solvents, propylene glycol monoalkyl ether acetates, acyclic or cyclic ketones, lactic acid esters, 3-alkoxypropionic acid esters and the like are preferred in that favorable film intra-plane uniformity can be secured in coating. The solvent may be used either alone, or as a mixture of two or more types thereof.

In addition, other solvent may be used as needed together with the solvent described above, such as a solvent having a high boiling point like e.g., benzylethyl ether, di-n-hexyl ether, diethylene glycol monomethyl ether, diethylene glycol monoethyl ether, acetonyl acetone, isophorone, caproic acid, caprylic acid, 1-octanol, 1-nonanol, benzyl alcohol, benzyl acetate, ethyl benzoate, diethyl oxalate, diethyl maleate, ethylene carbonate, propylene carbonate, ethylene glycol monophenyl ether acetate, or the like.

The other solvent may be used either alone, or as a mixture of two or more thereof. The proportion of the other solvent used is typically no greater than 50% by mass, and preferably no greater than 30% by mass with respect to the total of the solvent.

The total amount of the solvent used corresponds to an amount that makes the total solid content of the radiation-sensitive composition solution be typically 5 to 50% by mass, preferably 10 to 50% by mass, more preferably 10 to 40% by mass, still more preferably 10 to 30% by mass, and particularly preferably 10 to 25% by mass. When the total solid content of the solution falls within the above range, favorable uniformity can be secured in coating.

Formation of Resist Pattern

When a resist pattern is formed from the radiation-sensitive resin composition of the embodiment of the present invention, a solution of the radiation-sensitive resin composition prepared as described above is applied on a substrate such as, for example, a silicon wafer or a wafer covered with aluminum by an appropriate coating means such as spin-coating, cast coating or roll coating to form a resist film. Thereafter, after a heating treatment (hereinafter, may be also referred to as "PB") is carried out beforehand as the case may be, the resist film is exposed through a predetermined mask pattern.

The radioactive ray which may be used in the exposure is exemplified by far ultraviolet rays such as a bright line spectrum in a mercury lamp (wavelength: 254 nm), a KrF excimer laser (wavelength: 248 nm), an ArF excimer laser (wavelength: 193 nm), an $F_2$ excimer laser (wavelength: 157 nm), and EUV light (wavelength: 13 nm, etc.), as well as X-rays such as synchrotron radioactive rays, charged particle-rays such as electron beams, and the like. The radioactive ray is preferably a far ultraviolet ray and a charged particle-ray. More preferably, the radioactive ray is a KrF excimer laser (wavelength: 248 nm), an ArF excimer laser (wavelength: 193 nm), an $F_2$ excimer laser (wavelength: 157 nm) and electron beams, in accordance with the type of the radiation-sensitive acid generating agent employed. Alternatively, liquid immersion lithography may be also carried out by placing a liquid for liquid immersion lithography placed on a resist film, and then exposing resist film through the liquid for liquid immersion lithography.

Conditions for exposure such as radiation dose may be determined ad libitum depending on the compositional formulation of the radiation-sensitive resin composition, the type of the additive, and the like. Additionally, in forming the resist pattern, it is preferable to carry out a heat treatment after the exposure (hereinafter, may be also referred to as "PEB") in light of improvement of apparent sensitivity of the resist. Heating conditions of the PEB may vary depending on the compositional formulation of the radiation-sensitive resin composition, the type of the additive, and the like, the temperature is typically 30 to 200° C., and preferably 50 to 150° C.

Thereafter, the exposed resist film is developed with an alkaline developer solution to form a predetermined positive type or negative type resist pattern.

As the alkaline developer solution, for example, an aqueous alkaline solution prepared by dissolving one or more alkaline compounds such as alkali metal hydroxide, ammonia water, alkylamines, alkanolamines, heterocyclic amines, tetraalkylammonium hydroxides, choline, 1,8-diazabicyclo[5.4.0]-7-undecene, and 1,5-diazabicyclo[4.3.0]-5-nonene may be used. Particularly preferred alkaline developer solution is an aqueous solution of tetraalkylammonium hydroxides.

The concentration of the aqueous alkaline solution is preferably no greater than 10% by mass, more preferably 1 to 10% by mass, and still more preferably 2 to 5% by mass. In this instance, when the concentration of the aqueous alkaline solution is no greater than 10% by mass, dissolution at a light-unexposed site (in the case of positive type) at a light-exposed site (in the case of negative type) in the alkaline developer can be suppressed.

An appropriate amount of a surfactant and the like may be preferably added to a developer solution consisting of the aqueous alkaline solution, whereby wettability of the alkaline developer solution with respect to the resist film can be improved. Note that after the development carried out with the developer solution constituted with the aqueous alkaline solution, in general, washing with water and drying will follow.

Radiation-Sensitive Acid Generating Agent

The radiation-sensitive acid generating agent of the embodiment of the present invention is characterized by including the compound (A) described in the foregoing. The radiation-sensitive acid generating agent of the embodiment of the present invention is suitably used for the radiation-sensitive resin composition of the embodiment of the present invention.

EXAMPLES

Hereinafter, the present invention will be specifically explained by way of Examples, but the present invention is not limited to these Examples. It is to be noted that the "%" in Examples and Comparative Examples is on molar basis unless otherwise stated particularly. Furthermore, methods for the determination of various types of physical property values, and evaluation methods of various characteristics are shown below.
Conditions of Evaluation:

Using the radiation-sensitive resin compositions of Examples and Comparative Examples, positive type resist patterns were formed using the pattern-forming method (P-1) or (P-2) described below, and each evaluation was made.
Pattern-Forming Method (P-1)

On a 12-inch silicon wafer having an underlayer antireflective film ("ARC66", manufactured by Nissan Chemical Industries, Ltd.) provided thereon, a coating film having a film thickness of 75 nm was provided by each radiation-sensitive resin composition, and thereafter subjected to pre-baking (PB) at a temperature shown in Table 1 for 60 sec. Next, the coating film was exposed through a mask pattern using an ArF excimer laser immersion Scanner ("NSR S610C", manufactured by NIKON Corporation) under a condition involving an NA of 1.3, a ratio of 0.800 and Annular. After the exposure, post-baking (PEB) was carried out at 95° C. for 60 sec. Thereafter, the coating film was developed with a 2.38% by mass aqueous tetramethylammonium hydroxide solution and washed with water, followed by drying to form a positive type resist pattern.
Pattern-Forming Method (P-2)

On a 12-inch silicon wafer having an underlayer antireflective film ("ARC66", manufactured by Nissan Chemical Industries, Ltd.) provided thereon, a coating film having a film thickness of 75 nm was provided by each radiation-sensitive resin composition, and thereafter subjected to PB at a temperature shown in Table 1 for 60 sec. Next, a composition for forming an upper layer film described in Example 1 of WO 2008/047678 was spin-coated on the coating film formed, and PB was carried out at 90° C. for 60 sec to form a coating film having a film thickness of 90 nm. This coating film was exposed through a mask pattern using an ArF excimer laser immersion Scanner ("NSR S610C", manufactured by NIKON Corporation) under a condition involving an NA of 1.3, a ratio of 0.800 and Annular. After the exposure, post-baking (PEB) was carried out at a temperature shown in Table 1 for 60 sec. Thereafter, the coating film was developed with a 2.38% by mass aqueous tetramethylammonium hydroxide solution and washed with water, followed by drying to form a positive type resist pattern.
MEEF An exposure dose at which a line-and-space (LS) pattern having a line width of 50 nm was formed by exposing through a 1 L/1 S mask pattern with a target size of 50 nm under the condition for pattern formation described above was defined as "optimal exposure dose". Then an LS pattern having a pitch of 100 nm was formed at this optimal exposure dose using each mask pattern with a target size of the line width of 46 nm, 48 nm, 50 nm, 52 nm or 54 nm, and the line width formed on the resist film was measured with an SEM for line-width measurement (CG4000, manufactured by Hitachi, Ltd.). In this procedure, the line width (nm) formed on the resist film using each mask pattern was plotted along the ordinate with respect to the target size (nm) along the abscissa, and the slope of the resulting straight line was determined as MEEF performance.
LWR An exposure dose at which a resist pattern having a line width of 50 nm was formed by exposing through a 1 L/1.8 S mask pattern with a target size of 50 nm under the condition for pattern formation described above was defined as "optimal exposure dose". In the observation of the pattern with a line width of 50 nm obtained at the optimal exposure dose, line widths at arbitrary ten points were measured when observed from above the pattern using a SEM for critical dimension measurement: CG4000 manufactured by Hitachi, Ltd., and the variance of measurements expressed as a value in terms of the 3 Sigma was defined as "LWR". The lower LWR value indicates more favorable linearity of the pattern.
Minimum Collapse Dimension The exposure was carried out through a 1 L/1.8 S mask pattern with a target size of 50 nm under the condition for pattern formation described above while changing the exposure dose by 1 mJ. The line width of the pattern formed at an exposure dose less than the exposure dose at which the line collapse occurred by 1 mJ was measured with a SEM for critical dimension measurement (model "CG4000" manufactured by Hitachi, Ltd.,). The line width measured was defined as a minimum collapse dimension. Note that the smaller value thus determined indicates more superior resistance to pattern collapse.

Synthesis Example 1

A monomer solution was prepared by dissolving 31.63 g (35 mol %) of compound (S-1) described below, 49.60 g (45 mol %) of compound (S-3) described below, 6.45 g (10 mol %) of compound (S-4) described below in 200 g of 2-butanone and further charging thereto 8.14 g of 2,2'-azobis(2-methylpropionitrile). A 1,000 mL three-neck flask which had been charged with 12.32 g (10 mol %) of compound (S-2) described below and 100 g of 2-butanone was purged with nitrogen for 30 min. After the nitrogen purge, the reaction vessel was heated to 80° C. with stirring, and the monomer solution prepared beforehand was added dropwise thereto over 3 hrs using a dripping funnel. A time point at which the dropwise addition was started was defined as a polymerization starting time, and the polymerization reaction was performed for 6 hrs. After the completion of the polymerization, the polymerization solution was cooled to no higher than 30° C. by water-cooling, and charged into 4,000 g of methanol. The white powder thus precipitated was filtered off. The white powder obtained by filtration was dispersed in 400 g of methanol to give a slurry state, followed by washing and filtration. Such an operation was repeated twice, and thereafter vacuum dried at 50° C. for 17 hrs to obtain a copolymer (resin (B-1)) as a white powder. The copolymer had an Mw of 4,300 and Mw/Mn of 1.30. As a result of a $^{13}$C-NMR analysis, the copolymer had a content of each of the structure units derived from the compound (S-1), the compound (S-2), the compound (S-3) and the compound (S-4) of 35.6:8.9:46.2:9.3 (mol %). The copolymer is designated as polymer (B-1).

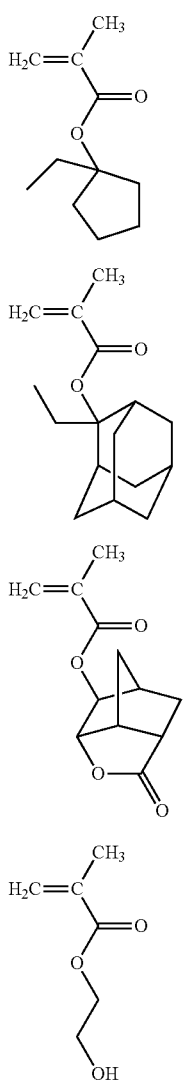

(S-1)

(S-2)

(S-3)

(S-4)

Synthesis Example 2

A monomer solution was prepared by dissolving 37.41 g (40 mol %) of compound (S-5) described below and 62.59 g (60 mol %) of compound (S-6) described below in 100 g of 2-butanone and further charging thereto 4.79 g of 2,2'-azobis (2-methylpropionitrile). A 1,000 mL three-neck flask which had been charged with 100 g of 2-butanone was purged with nitrogen for 30 min. After the nitrogen-purge, the reaction vessel was heated to 80° C. with stirring, and the monomer solution prepared beforehand was added dropwise thereto over 3 hrs using a dripping funnel. A time point at which the dropwise addition was started was defined as a polymerization starting time, and the polymerization reaction was performed for 6 hrs. After the completion of the polymerization, 150 g of 2-butanone was removed in vacuo from the polymerization solution. After cooling to no higher than 30° C., the polymerization solution was charged into a mixed solvent of 900 g of methanol and 100 g of ultra pure water. The white powder thus precipitated was filtered off. The white powder obtained by filtration was dispersed in 100 g of methanol to give a slurry state, followed by washing and filtration. Such an operation was repeated twice. The resultant white powder was dried in vacuo at 50° C. for 17 hrs to give a copolymer (78 g, yield: 78%). The copolymer had an Mw of 6,920 and Mw/Mn of 1.592. As a result of a $^{13}$C-NMR analysis, the copolymer had a content of each of the structure units derived from the compound (S-5) and the compound (S-6) of 40.8: 59.2 (mol %). The fluorine content was 9.6% by mass. The copolymer is designated as polymer (C-1).

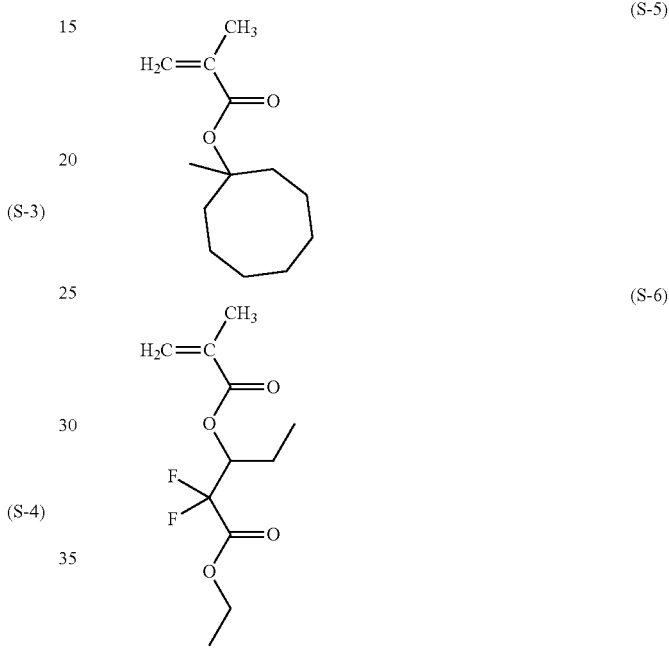

(S-5)

(S-6)

Preparation of Radiation-Sensitive Resin Composition

Components other than the base polymer (B) and the polymer (C) of the radiation-sensitive resin composition used in each Example and Comparative Example are as follows. Some of the components are shown together with the chemical formula thereof.

Acid Generating Agent (compound (A))

(A-1): compound represented by the following formula

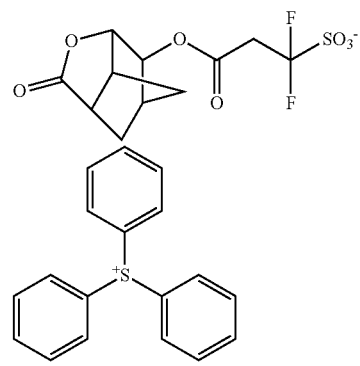

(A-2): compound represented by the following formula

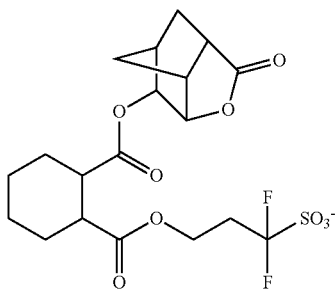

(A-3): triphenylsulfonium 4-(1-adamantanecarbonyloxy)-1,1,2,2-tetrafluorobutanesulfonate (compound represented by the following formula)

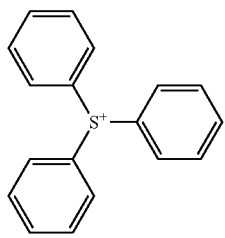

Acid Diffusion Control Agent (D)

(D-1) triphenylsulfonium 2-hydroxybenzoate (compound represented by the following formula)

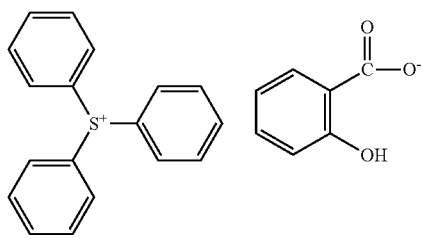 [SMILES: c1ccc([S+](c2ccccc2)c2ccccc2)cc1 ; O=C([O-])c1ccccc1O]

(D-2) tert-butyl-4-hydroxy-1-piperidine carboxylate (compound represented by the following formula)

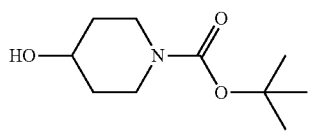

Solvent (E)

(E-1) propylene glycol methyl ether acetate (E-2) cyclohexanone

Lactone Compound (G-1) γ-butyrolactone

Example 1

The polymer (B-1) in an amount of 100 parts by mass as the base polymer (B), 13 parts by mass of the acid generating agent (A-1) as the acid generating agent (the compound (A)), 13 parts by mass of (D-1) as the acid diffusion control agent (D), 3 parts by mass of the polymer (C-1) as the polymer (C), 1980 parts by mass of (E-1) and 848 parts by mass of (E-2) as the solvent (E), and 200 parts by mass of (G-1) were added and the components were mixed to give a homogenous solution. Thereafter, the solution was filtrated through a membrane filter having a pore size of 200 nm to prepare a positive type radiation-sensitive composition (concentration of total solid contents: about 4%). Each composition thus obtained was used to form a pattern according to the pattern-forming method (P-2) described above, and evaluated on MEEF, LWR and Minimum collapse dimension under the conditions of evaluation described above. The results are shown in Table 1 all together.

Examples 2 to 6, and Comparative Examples 1 to 4

Positive type radiation-sensitive resin compositions were prepared in a similar manner to Example 1 except that except that each formulation was as shown in Table 1. Results of each evaluation are shown in Table 1 together with. It is to be noted that in the conditions of evaluation for Examples 2, 3, and Comparative Examples 1 and 2, the aforementioned pattern-forming method (P-2) was employed similarly to Example 1, whereas in the conditions of evaluation for Examples 4, 5 and 6, and Comparative Examples 3 and 4, the aforementioned pattern-forming method (P-1) was employed. In Table 1, "-" designates that the relevant component was not used.

TABLE 1

| | (A) Component | | (B) Base polymer | | (C) Polymer | | (D) Acid diffusion control agent | | Lactone compound G-1 parts by mass | PB (°C.) | PEB (°C.) | Results of evaluation | | |
|---|---|---|---|---|---|---|---|---|---|---|---|---|---|---|
| | type | parts by mass | type | parts by mass | type | parts by mass | type | parts by mass | | | | MEEF | LWR (nm) | Minimum collapse dimension (nm) |
| Example 1 | A-1 | 13 | B-1 | 14 | C-1 | 3 | D-1 | 13 | 200 | 120 | 85 | 3.0 | 4.1 | 30 |
| Example 2 | A-1 | 12 | B-1 | 14 | C-1 | 3 | D-2 | 16 | 200 | 110 | 90 | 3.2 | 4.1 | 30 |
| Example 3 | A-2 | 13 | B-1 | 14 | C-1 | 3 | D-1 | 13 | 200 | 100 | 110 | 2.9 | 3.8 | 29 |
| Example 4 | A-1 | 13 | B-1 | 14 | C-1 | — | D-1 | 13 | — | 120 | 85 | 2.9 | 4.0 | 28 |
| Example 5 | A-1 | 12 | B-1 | 14 | C-1 | — | D-2 | 16 | — | 110 | 90 | 3.0 | 4.4 | 28 |
| Example 6 | A-2 | 13 | B-1 | 14 | C-1 | — | D-1 | 13 | — | 100 | 110 | 2.9 | 4.1 | 29 |
| Comparative Example 1 | A-3 | 13 | B-1 | 14 | C-1 | 3 | D-1 | 13 | 200 | 120 | 85 | 3.5 | 5.4 | 39 |
| Comparative Example 2 | A-3 | 12 | B-1 | 14 | C-1 | 3 | D-2 | 16 | 200 | 110 | 90 | 3.7 | 6.0 | 39 |
| Comparative Example 3 | A-3 | 13 | B-1 | 14 | C-1 | — | D-1 | 13 | — | 120 | 85 | 3.4 | 5.5 | 39 |
| Comparative Example 4 | A-3 | 12 | B-1 | 14 | C-1 | — | D-2 | 16 | — | 110 | 90 | 3.6 | 6.0 | 38 |

As shown in Table 1, by using the radiation-sensitive resin composition of the embodiment of the present invention, formation of a pattern having improved LWR and minimum collapse dimension, accompanied by favorable balance with MEEF was enabled.

The radiation-sensitive resin composition of the embodiment of the present invention is useful for microfabrication in which various types of radioactive rays may be used which include far ultraviolet rays such as a KrF excimer laser and an ArF excimer laser, X-rays such as a synchrotron radioactive ray, charged particle rays such as an electron beam.

Specifically, the radiation-sensitive resin composition of the embodiment of the present invention is superior in transparency and sensitivity to far ultraviolet rays typified by a KrF excimer laser, an ArF excimer laser, an $F_2$ excimer laser and EUV, and to actinic radioactive rays such as an electron beam, and also has a favorable balance of resistance to pattern collapse after development, LWR and MEEF. Moreover, according to the radiation-sensitive acid generating agent of the embodiment of the present invention, a balance of resistance to pattern collapse after development, LWR and MEEF can be improved when used in a radiation-sensitive resin composition.

Obviously, numerous modifications and variations of the present invention are possible in light of the above teachings. It is therefore to be understood that within the scope of the appended claims, the invention may be practiced otherwise than as specifically described herein.

The invention claimed is:
1. A radiation-sensitive resin composition comprising:
a compound represented by a formula (1); and
a base polymer:

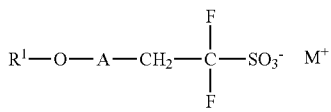

(1)

wherein, in the formula (1), A represents —CO— or —CH$_2$—; $R^1$ represents a group represented by a formula (a1); and $M^+$ represents a monovalent cation,

(a1)

wherein, in the formula (a1), $R^2$ represents a heterocyclic group having 3 to 30 ring atoms or a cyclic ketone group having 3 to 30 ring atoms; $R^3$ and $R^5$ each independently represent —CO—, —COO—, —OCO—, —NHCO—, —CONH or a combination thereof; $R^4$ represents a hydrocarbon group having 1 to 30 carbon atoms; m is an integer of 1 or 2; n is 1, wherein a part or all of hydrogen atoms included in the heterocyclic group and the cyclic ketone group represented by $R^2$, and the hydrocarbon group represented by $R^4$ may be unsubstituted or substituted, and wherein in a case where m is 2, a plurality of $R^3$s are each identical or different and a plurality of $R^4$s are each identical or different; and * denotes a binding site to —O— in the formula (1).

2. The radiation-sensitive resin composition according to claim 1, wherein $M^+$ in the formula (1) represents a sulfonium cation or an iodonium cation.

3. The radiation-sensitive resin composition according to claim 1, wherein the base polymer comprises a structural unit represented by a formula (2):

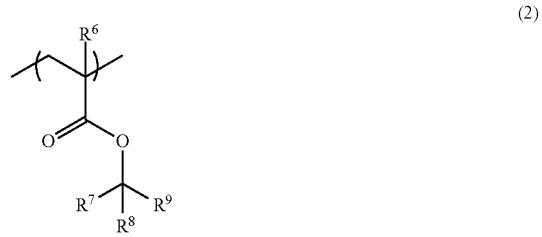

(2)

wherein, in the formula (2), $R^6$ represents a hydrogen atom or a methyl group; $R^7$ represents a linear or branched alkyl group having 1 to 4 carbon atoms, or an alicyclic hydrocarbon group having 4 to 20 carbon atoms; and $R^8$ and $R^9$ each independently represent a linear or branched alkyl group having 1 to 4 carbon atoms, or an alicyclic hydrocarbon group having 4 to 20 carbon atoms, or $R^8$ and $R^9$ taken together represent an alicyclic hydrocarbon group having 4 to 20 carbon atoms together with the carbon atom to which $R^8$ and $R^9$ bond.

4. The radiation-sensitive resin composition according to claim 1, wherein the heterocyclic group represented by $R^2$ includes a lactone structure, a cyclic carbonate structure, a cyclic sulfide structure, or a structure represented by a formula (d-1),

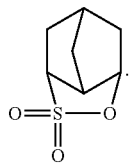

(d-1)

5. The radiation-sensitive resin composition according to claim 1, wherein, in the formula (a1), m is 1.

6. A radiation-sensitive acid generating agent comprising a compound represented by a formula (1):

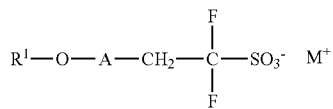

(1)

wherein, in the formula (1), A represents —CO— or —CH$_2$—; $R^1$ is a group represented by a formula (a1); and $M^+$ represents a monovalent cation,

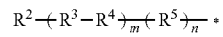

(a1)

wherein, in the formula (a1), $R^2$ represents a heterocyclic group having 3 to 30 ring atoms or a cyclic ketone group having 3 to 30 ring atoms; $R^3$ and $R^5$ each independently represent —CO—, —COO—, —OCO—, —NHCO—, —CONH or a combination thereof; $R^4$ represents a hydrocarbon group having 1 to 30 carbon atoms; m is an integer of 1 or 2; n is 1, wherein a part or all of hydrogen atoms included in the heterocyclic group and the cyclic ketone group represented by $R^2$, and the hydrocarbon group represented by $R^4$ may be unsubstituted or substituted, and wherein in a case where m is 2, a plurality of $R^3$s are each identical or different and a plurality of $R^4$s are each identical or different; and * denotes a binding site to —O— in the formula (1).

7. The radiation-sensitive acid generating agent according to claim 6, wherein the heterocyclic group represented by $R^2$ includes a lactone structure, a cyclic carbonate structure, a cyclic sulfide structure, or a structure represented by a formula (d-1),

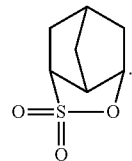

(d-1)

8. The radiation-sensitive acid generating agent according to claim 6, wherein, in the formula (a1), m is 1.

* * * * *